(12) United States Patent
Kim et al.

(10) Patent No.: US 9,446,130 B2
(45) Date of Patent: Sep. 20, 2016

(54) BTK INHIBITORS

(71) Applicant: MERCK SHARP & DOHME CORP., Rahway, NJ (US)

(72) Inventors: Ronald M. Kim, Summit, NJ (US); Jian Liu, Edison, NJ (US); Hao Wu, Shanghai (CN); Shilan Liu, Shanghai (CN); Chundao Yang, Shanghai (CN); Shuling Zheng, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/762,929

(22) PCT Filed: Jan. 17, 2014

(86) PCT No.: PCT/US2014/011950
§ 371 (c)(1),
(2) Date: Jul. 23, 2015

(87) PCT Pub. No.: WO2014/116504
PCT Pub. Date: Jul. 31, 2014

(65) Prior Publication Data
US 2015/0353565 A1 Dec. 10, 2015

(30) Foreign Application Priority Data
Jan. 23, 2013 (WO) ................ PCT/CN2013/070898

(51) Int. Cl.
C07D 487/04 (2006.01)
C07D 473/34 (2006.01)
A61K 31/519 (2006.01)
A61K 31/4985 (2006.01)
A61P 19/02 (2006.01)
A61K 45/06 (2006.01)
C07D 519/00 (2006.01)

(52) U.S. Cl.
CPC ........... *A61K 45/06* (2013.01); *A61K 31/4985* (2013.01); *A61K 31/519* (2013.01); *C07D 473/34* (2013.01); *C07D 487/04* (2013.01); *C07D 519/00* (2013.01)

(58) Field of Classification Search
CPC C07D 471/04; C07D 473/04; C07D 487/04; A61K 31/4985; A61K 31/519
USPC ........................ 544/262, 281; 514/249, 262.1
See application file for complete search history.

(56) References Cited

U.S. PATENT DOCUMENTS 6,921,763 B2 7/2005 Hirst et al.
2009/0258874 A1 10/2009 Revesz
2009/0286768 A1 11/2009 Crew et al.
2009/0325956 A1 12/2009 Taniguchi et al.
2012/0309966 A1 12/2012 de Man et al.

FOREIGN PATENT DOCUMENTS

| WO | WO2011095556 A1 | 8/2011 |
| WO | WO2013010380 A1 | 1/2013 |
| WO | WO2013010868 | 1/2013 |
| WO | WO2013010869 | 1/2013 |
| WO | WO2014113932 | 7/2014 |
| WO | WO2014114185 | 7/2014 |

OTHER PUBLICATIONS

Whang et al., Drug Discovery Today, pp. 1-5, 2014.*
Akinleye et al. Journal of Hematology & Oncology 2013, 6:59.*
Chakravarty et al. Clinical Immunology (2013) 148, 66-78.*

* cited by examiner

*Primary Examiner* — Venkataraman Balasubramanian
(74) *Attorney, Agent, or Firm* — Matthew A. Leff; John C. Todaro

(57) ABSTRACT

The present invention provides Bruton's Tyrosine Kinase (Btk) inhibitor compounds according to Formula I or pharmaceutically acceptable salts thereof. Formula I or a pharmaceutically acceptable salt thereof or to pharmaceutical compositions comprising these compounds and to their use in therapy. In particular, the present invention relates to the use of Btk inhibitor compounds in the treatment of Btk mediated disorders.

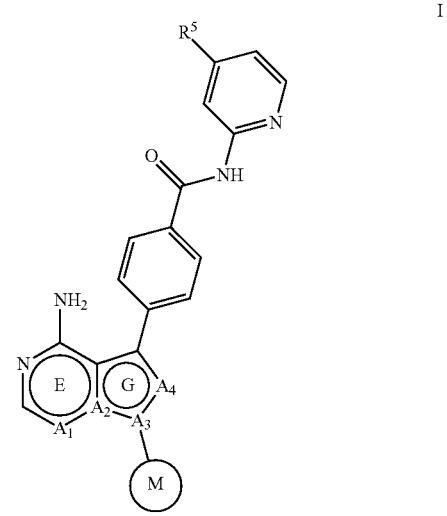

18 Claims, No Drawings

BTK INHIBITORS

FIELD OF THE INVENTION

The present invention relates to Btk inhibitor compounds, to pharmaceutical compositions comprising these compounds and to their use in therapy. In particular, the present invention relates to the use of Btk inhibitor compounds in the treatment of Bruton's Tyrosine Kinase (Btk) mediated disorders.

BACKGROUND OF THE INVENTION

B lymphocyte activation is key in the generation of adaptive immune responses. Derailed B lymphocyte activation is a hallmark of many autoimmune diseases and modulation of this immune response is therefore of therapeutic interest. Recently the success of B cell therapies in autoimmune diseases has been established. Treatment of rheumatoid arthritis (RA) patients with Rituximab (anti-CD20 therapy) is an accepted clinical therapy by now. More recent clinical trial studies show that treatment with Rituximab also ameliorates disease symptoms in relapsing remitting multiple sclerosis (RRMS) and systemic lupus erythematosus (SLE) patients. This success supports the potential for future therapies in autoimmune diseases targeting B cell immunity.

Bruton tyrosine kinase (Btk) is a Tec family non-receptor protein kinase, expressed in B cells and myeloid cells. The function of Btk in signaling pathways activated by the engagement of the B cell receptor (BCR) and FcεR1 on mast cells is well established. In addition, a function for Btk as a downstream target in Toll like receptor signaling was suggested. Functional mutations in Btk in human results in the primary immunodeficiency disease called XLA which is characterized by a defect in B cell development with a block between pro- and pre-B cell stage. This results in an almost complete absence of B lymphocytes in human causing a pronounced reduction of serum immunoglobulin of all classes. These finding support the key role for Btk in the regulation of the production of auto-antibodies in autoimmune diseases. In addition, regulation of Btk may affect BCR-induced production of pro-inflammatory cytokines and chemokines by B cells, indicating a broad potential for Btk in the treatment of autoimmune diseases.

With the regulatory role reported for Btk in FcεR-mediated mast cell activation, Btk inhibitors may also show potential in the treatment of allergic responses [Gillian et al, Immunological Reviews 288 (2009) pp 149-169].
Furthermore, Btk is also reported to be implicated in RANKL-induced osteoclast differentiation [Shinohara et al, Cell 132 (2008) pp 794-806] and therefore may also be of interest for the treatment of bone resorption disorders.

Other diseases with an important role for dysfunctional B cells are B cell malignancies. Indeed anti-CD20 therapy is used effectively in the clinic for the treatment of follicular lymphoma, diffuse large B-cell lymphoma and chronic lymphocytic leukemia [Lim et al, Haematologica, 95 (2010) pp 135-143]. The reported role for Btk in the regulation of proliferation and apoptosis of B cells indicates there is potential for Btk inhibitors in the treatment of B cell lymphomas as well. Inhibition of Btk seems to be relevant in particular for B cell lymphomas due to chronic active BCR signaling [Davis et al, Nature, 463 (2010) pp 88-94].

Some classes of Btk inhibitor compounds have been described as kinase inhibitors e.g. Imidazo[1,5-f][1,2,4]triazine compounds have been described in WO2005097800 and WO2007064993. Imidazo[1,5-a]pyrazine compounds have been described in WO2005037836 and WO2001019828 as IGF-1R enzyme inhibitors.

Some of the Btk inhibitors reported are not selective over Src-family kinases. With dramatic adverse effects reported for knockouts of Src-family kinases, especially for double and triple knockouts, this is seen as prohibitive for the development of Btk inhibitors that are not selective over the Src-family kinases.

Both Lyn-deficient and Fyn-deficient mice exhibit autoimmunity mimicking the phenotype of human lupus nephritis. In addition, Fyn-deficient mice also show pronounced neurological defects. Lyn knockout mice also show an allergic-like phenotype, indicating Lyn as a broad negative regulator of the IgE-mediated allergic response by controlling mast cell responsiveness and allergy-associated traits [Odom et al, J. Exp. Med., 199 (2004) pp 1491-1502]. Furthermore, aged Lyn knock-out mice develop severe splenomegaly (myeloid expansion) and disseminated monocyte/macrophage tumors [Harder et al, Immunity, 15 (2001) pp 603-615]. These observations are in line with hyperresponsive B cells, mast cells and myeloid cells, and increased Ig levels observed in Lyn-deficient mice. Female Src knockout mice are infertile due to reduced follicle development and ovulation [Roby et al, Endocrine, 26 (2005) pp 169-176]. The double knockouts $Src^{-/-}Fyn^{-/-}$ and $Src^{-/-}Fyn^{-/-}Yes^{-/-}$ show a severe phenotype with effects on movement and breathing. The triple knockouts $Src^{-/-}Fyn^{-/-}Yes^{-/-}$ die at day 9.5 [Klinghoffer et al, EMBO J., 18 (1999) pp 2459-2471]. For the double knockout $Src^{-/-}Hck^{-/-}$, two thirds of the mice die at birth, with surviving mice developing osteopetrosis, extramedullary hematopoiesis, anemia, leukopenia [Lowell et al, Blood, 87 (1996) pp 1780-1792].

Hence, an inhibitor that inhibits multiple or all kinases of the Src-family kinases simultaneously may cause serious adverse effects.

SUMMARY OF THE INVENTION

The present invention provides compounds which inhibit Btk activity, their use for treatment of Btk mediated diseases and disorders, in particular autoimmune diseases and inflammatory diseases, as well as pharmaceutical compositions comprising such compounds and pharmaceutical carriers.

DETAILED DESCRIPTION

The object of the present invention is to provide Bruton's Tyrosine Kinase (Btk) inhibitor compounds, to pharmaceutical compositions comprising these compounds and to their use in therapy. In particular, the present invention relates to the use of Btk inhibitor compounds in the treatment of Btk mediated disorders.

More specifically, the present invention provides Btk inhibitor compounds according to Formula I or pharmaceutically acceptable salts thereof Formula I

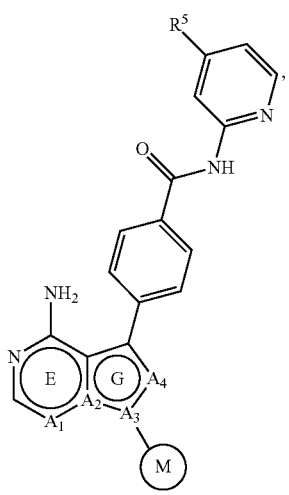

wherein:

A₁, A₂, A₃, and A₄ are independently C, CH, or N and bicyclic ring system E-G is selected from the group consisting of:

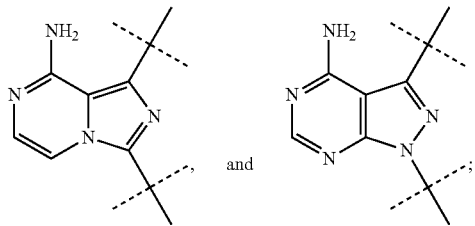

R⁵ is H, cyano, (1-4C)alkyl, (1-5C)alkoxy; any alkyl group of R⁵ may optionally be substituted with one, two or three halogen;

ring system M is selected from the group consisting of:

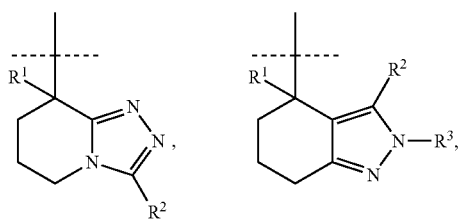

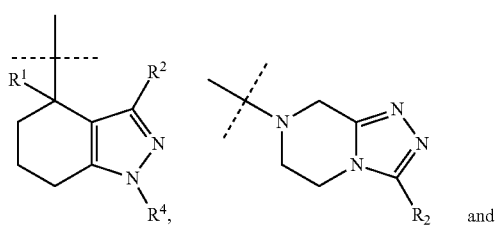

-continued

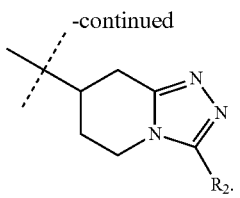

R¹ is H or OH;
R² is H, (1-3C)alkyl, cyclopropyl, or CF₃; and
R³ and R⁴ are each independently selected from H, (1-3C)alkyl, (1-3C)alkoxy, and hydroxyl(1-3C)alkyl.

The terms as used herein refer to the following:

Halogen means fluorine, chlorine, bromine or iodine. Fluorine, chlorine or bromine being preferred halogens, fluorine or chlorine being more preferred.

(1-3C)Alkyl means a branched or unbranched alkyl group having 1-3 carbon atoms, being methyl, ethyl, propyl or isopropyl.

(1-3C)Alkoxy means an alkoxy group having 1-3 carbon atoms, the alkyl moiety having the same meaning as previously defined. (1-2C)alkoxy groups are preferred.

(1-4C)Alkoxy means an alkoxy group having 1-4 carbon atoms, the alkyl moiety having the same meaning as previously defined. (1-3C)alkoxy groups are preferred, (1-2C)alkoxy groups being most preferred.

(1-5C)Alkoxy means an alkoxy group having 1-5 carbon atoms, the alkyl moiety having the same meaning as previously defined. (1-4C)alkoxy groups are preferred, (1-3C)alkoxy groups being more preferred.

(1-6C)Alkoxy means an alkoxy group having 1-6 carbon atoms, the alkyl moiety having the same meaning as previously defined. (1-5C)alkoxy groups are preferred, (1-4C)alkoxy groups being more preferred.

(3-6C)Cycloalkyl means a cycloalkyl group having 3-6 carbon atoms, being cyclopropyl, cyclobutyl, cyclopentyl or cyclohexyl. cyclopropyl, cyclobutyl, cyclopentyl being preferred.

(1-4C)Alkoxy(1-6C)alkyl means an alkyl group having 1-6 carbon atoms with the same meaning as previously defined, substituted with an alkoxy group the alkyl moiety of which having 1-4 carbon atoms as previously defined. Examples of "alkoxyalkyl" include, but are not limited to, methoxymethyl, 1-methoxyethyl, 2-ethoxyethyl, and 1,1-dimethoxyethyl.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

A circle in a ring of Formula I indicates that the ring is aromatic.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

The term pharmaceutically acceptable salt is well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

Aspects of the Invention

In one aspect the invention relates to a compound according to Formula I wherein $R^5$ is selected from the group consisting of hydrogen, fluorine, chlorine, CN, cyclopropyl, (1-3C)alkyl and (1-2C) alkoxy; the (1-3C)alkyl group of which is optionally substituted with one or more halogen.

In another aspect the invention relates to a compound of Formula I wherein $R^5$ is selected from the group consisting of $CF_3$, CN and

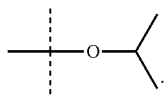

In another aspect the invention relates to a compound of Formula I wherein bicyclic ring system E-G is

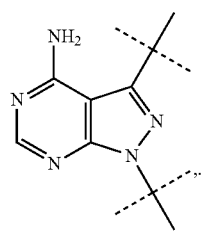

In another aspect the invention relates to a compound of Formula I wherein bicyclic ring system E-G is

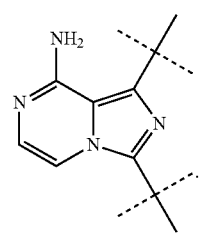

In another aspect the invention relates to a compound of Formula I wherein ring system M is selected from the group consisting of:

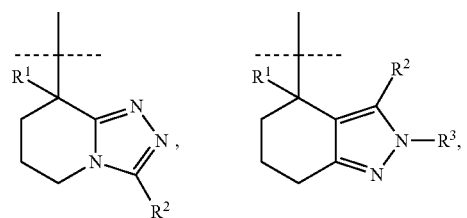

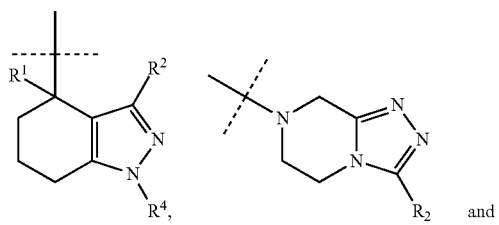

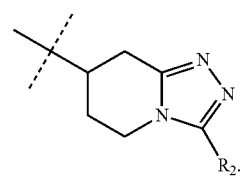

In another aspect the invention relates to a compound having Formula Ia

Formula Ia

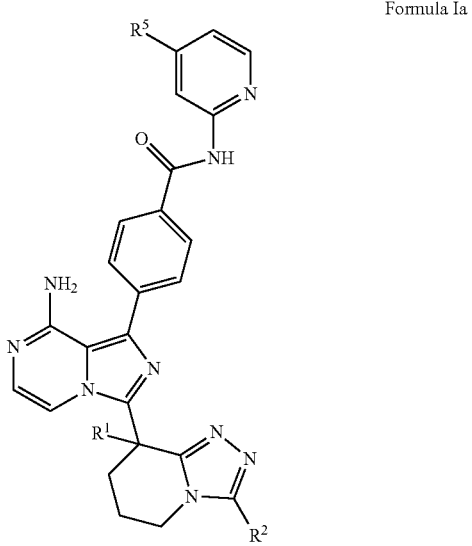

or a pharmaceutically acceptable salt or solvate thereof.

In another aspect the invention relates to a compound having Formula Ib1

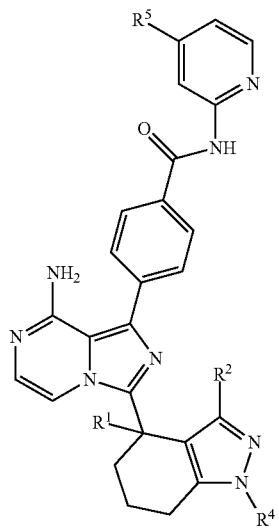

Formula Ib1 or a pharmaceutically acceptable salt or solvate thereof.

In another aspect the invention relates to a compound having Formula Ib2

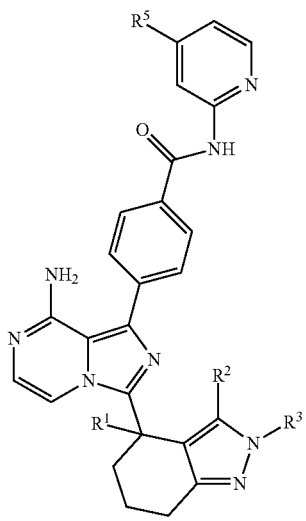

Formula Ib2 or a pharmaceutically acceptable salt or solvate thereof.

In another aspect the invention relates to a compound having Formula Ic

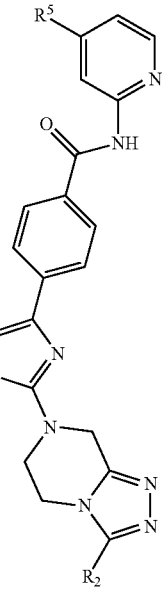

Formula Ic or a pharmaceutically acceptable salt or solvate thereof.

In another aspect the invention relates to a compound having Formula Id

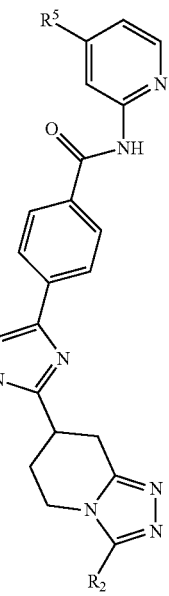

Formula Id or a pharmaceutically acceptable salt or solvate thereof.

In another aspect the invention relates to a compound having Formula Ie

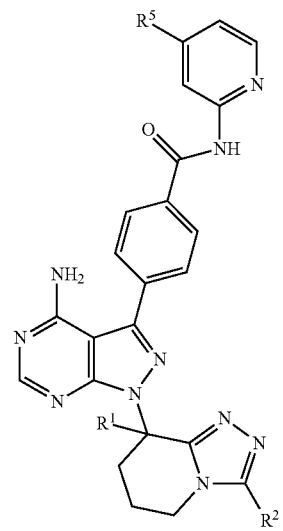

Formula Ie or a pharmaceutically acceptable salt or solvate thereof.

In another aspect the invention relates to a compound having Formula If1

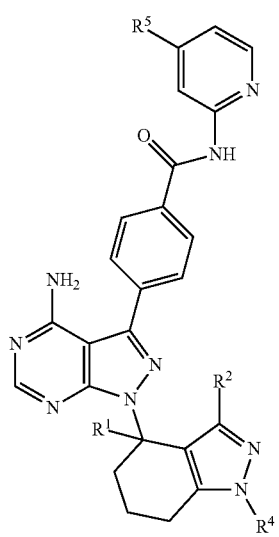

Formula If1 or a pharmaceutically acceptable salt or solvate thereof.

In another aspect the invention relates to a compound having Formula If2

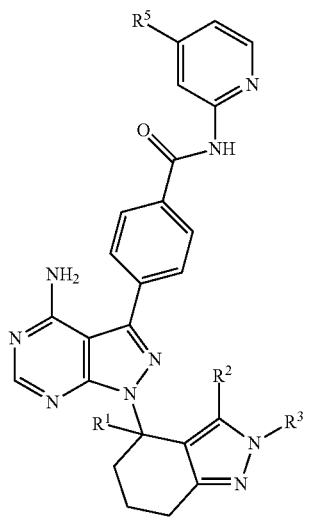

Formula If2 or a pharmaceutically acceptable salt or solvate thereof.

In another aspect the invention relates to a compound having Formula Ig

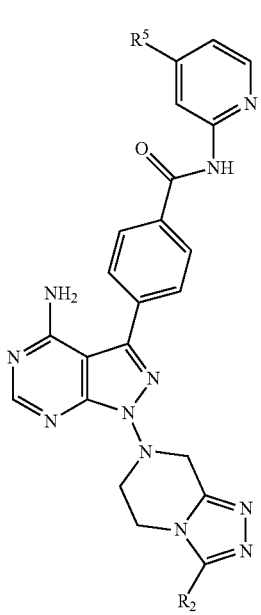

Formula Ig or a pharmaceutically acceptable salt or solvate thereof.

In another aspect the invention relates to a compound having Formula Ih

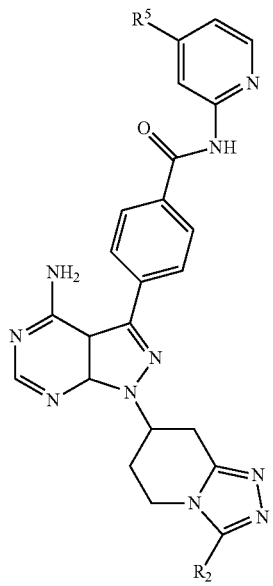

Formula Ih or a pharmaceutically acceptable salt or solvate thereof.

The invention also relates to those compounds wherein all specific definitions for $A_1$-$A_6$, $R^1$, $R^2$, $R^3$, $R^4$, and $R^5$, and all substituent groups in the various aspects of the inventions defined here above occur in any combination within the definition of the Btk inhibitor compounds of Formula I or pharmaceutically acceptable salts thereof.

In still another aspect the invention relates to a compound according to Formula I or a pharmaceutically acceptable salt or solvate thereof selected from the group consisting of:

4-[8-amino-3-(4-hydroxy-1-methyl-4,5,6,7-tetrahydro-1H-indazol-4-yl)imidazo[1,5-a]pyrazin-1-yl]-N-[4-(trifluoromethyl)pyridin-2-yl]benzamide;

4-{8-amino-3-[(4S)-4-hydroxy-1-methyl-4,5,6,7-tetrahydro-1H-indazol-4-yl]imidazo[1,5-a]pyrazin-1-yl}-N-[4-(trifluoromethyl)pyridin-2-yl]benzamide;

4-{8-amino-3-[(4R)-4-hydroxy-1-methyl-4,5,6,7-tetrahydro-1H-indazol-4-yl]imidazo[1,5-a]pyrazin-1-yl}-N-[4-(trifluoromethyl)pyridin-2-yl]benzamide;

4-[8-amino-3-(1-ethyl-4-hydroxy-4,5,6,7-tetrahydro-1H-indazol-4-yl)imidazo[1,5-a]pyrazin-1-yl]-N-[4-(trifluoromethyl)pyridin-2-yl]benzamide;

4-{4-amino-1-[(4S)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4R)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4R)-1-methyl-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4S)-2-methyl-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4S)-1-methyl-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4R)-2-methyl-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4S)-1-ethyl-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4S)-2-ethyl-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4R)-1-ethyl-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4R)-2-ethyl-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4S)-1-(2-hydroxyethyl)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4S)-2-(2-hydroxyethyl)-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4R)-1-(2-hydroxyethyl)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4R)-2-(2-hydroxyethyl)-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{8-amino-3-[(8R)-3-cyclopropyl-5,6,7,8-tetrahydro[1,2,4]triazolo[4,3-a]pyridin-8-yl]imidazo[1,5-a]pyrazin-1-yl}-N-[4-(trifluoromethyl)pyridin-2-yl]benzamide;

4-{8-amino-3-[(8S)-3-cyclopropyl-5,6,7,8-tetrahydro[1,2,4]triazolo[4,3-a]pyridin-8-yl]imidazo[1,5-a]pyrazin-1-yl}-N-[4-(trifluoromethyl)pyridin-2-yl]benzamide;

4-{8-amino-3-[(7S)-3-(trifluoromethyl)-5,6,7,8-tetrahydro[1,2,4]triazolo[4,3-a]pyridin-7-yl]imidazo[1,5-a]pyrazin-1-yl}-N-[4-(trifluoromethyl)pyridin-2-yl]benzamide;

4-{8-amino-3-[(7R)-3-(trifluoromethyl)-5,6,7,8-tetrahydro[1,2,4]triazolo[4,3-a]pyridin-7-yl]imidazo[1,5-a]pyrazin-1-yl}-N-[4-(trifluoromethyl)pyridin-2-yl]benzamide;

4-{8-amino-3-[(4R)-1-methyl-4,5,6,7-tetrahydro-1H-indazol-4-yl]imidazo[1,5-a]pyrazin-1-yl}-N-[4-(trifluoromethyl)pyridin-2-yl]benzamide;

4-{8-amino-3-[(4S)-1-methyl-4,5,6,7-tetrahydro-1H-indazol-4-yl]imidazo[1,5-a]pyrazin-1-yl}-N-[4-(trifluoromethyl)pyridin-2-yl]benzamide; and 4-{8-amino-3-[3-(trifluoromethyl)-5,6-dihydro[1,2,4]triazolo[4,3-a]pyrazin-7(8H)-yl]imidazo[1,5-a]pyrazin-1-yl}-N-[4-(1-methylethoxyl)pyridin-2-yl]benzamide.

The Btk inhibitor compounds of the invention having Formula I inhibit the Btk kinase activity. All compounds of the invention have an IC50 of 10 μM or lower. In another aspect the invention relates to compounds of Formula I which have an IC50 of less than 100 nM. In yet another aspect the invention relates to compounds of Formula I which have an IC50 of less than 10 nM.

The term IC50 means the concentration of the test compound that is required for 50% inhibition of its maximum effect in vitro.

In another aspect the invention relates to compounds of Formula I or pharmaceutically acceptable salts thereof, which have an IC50 of less than 100 nM. In yet another aspect the invention relates to the compounds of Formula I or pharmaceutically acceptable salts thereof, which have an IC50 of less than 10 nM.

The term IC50 means the concentration of the test compound that is required for 50% inhibition of its maximum effect in vitro.

Inhibition of kinase activity can be measured using the Immobilized Metal Assay for Phosphochemicals (IMAP) assay. IMAP is a homogeneous fluorescence polarization (FP) assay based on affinity capture of phosphorylated peptide substrates. IMAP uses fluorescein-labeled peptide substrates that, upon phosphorylation by a protein kinase, bind to so-called IMAP nanoparticles, which are derivatized with trivalent metal complexes. Binding causes a change in the rate of the molecular motion of the peptide, and results in an increase in the FP value observed for the fluorescein label attached to the substrate peptide (Gaudet et al. A homogeneous fluorescence polarization assay adaptable for a range of protein serine/threonine and tyrosine kinases. *J. Biomol. Screen* (2003) 8, 164-175).

Also BTK enzymatic activity was determined with the LANCE (Lanthanide Chelate Excite) TR-FRET (Time-resolved fluorescence resonance energy transfer) assay. In this assay, the potency ($IC_{50}$) of each compound was determined from an eleven point (1:3 serial dilution; final compound concentration range in assay from 1 μM to 0.017 nM) titration curve using the following outlined procedure. To each well of a black non-binding surface Corning 384-well microplate (Corning Catalog #3820), 5 nL of compound (2000 fold dilution in final assay volume of 10 μL) was dispensed, followed by the addition of 7.5 μL of 1× kinase buffer (50 mM Hepes 7.5, 10 mM $MgCl_2$, 0.01% Brij-35, 1 mM EGTA, 0.05% BSA & 1 mM DTT) containing 10.18 pg/μL (133.3 pM) of BTK enzyme (recombinant protein from baculovirus-transfected Sf9 cells: full-length BTK, 6HIS-tag cleaved). Following a 60 minute compound & enzyme incubation, each reaction was initiated by the addition of 2.5 μL 1× kinase buffer containing 8 μM biotinylated "A5" peptide (Biotin-EQEDEPEGDYFEWLE-NH2), and 100 μM ATP. The final reaction in each well of 10 μL consists of 100 pM hBTK, 2 μM biotin-A5-peptide, and 25 μM ATP. Phosphorylation reactions were allowed to proceed for 120 minutes. Reactions were immediately quenched by the addition of 20 uL of 1× quench buffer (15 mM EDTA, 25 mM Hepes 7.3, and 0.1% Triton X-100) containing detection reagents (0.626 nM of LANCE-Eu-W1024-anti-phosphoTyrosine antibody, PerkinElmer and 86.8 nM of Streptavidin-conjugated Dylight 650, Dyomics/Thermo-Fisher Scientific). After 60 minutes incubation with detection reagents, reaction plates were read on a PerkinElmer EnVision plate reader using standard TR-FRET protocol. Briefly, excitation of donor molecules (Eu-chelate:anti-phospho-antibody) with a laser light source at 337 nm produces energy that can be transferred to Dylight-650 acceptor molecules if this donor:acceptor pair is within close proximity. Fluorescence intensity at both 665 nm (acceptor) and 615 nm (donor) are measured and a TR-FRET ratio calculated for each well (acceptor intensity/donor intensity). $IC_{50}$ values were determined by 4 parameter robust fit of TR-FRET ratio values vs. ($Log_{10}$) compound concentrations.

The Btk activity can also be determined in B cell lines such as Ramos cells or in primary cell assays, e.g. PBMC or whole blood from human, monkey, rat or mouse or isolated splenocytes from monkey, rat or mouse. Inhibition of Btk activity can be investigated measuring anti-IgM-induced MIP1β production (Ramos, PBMC, splenocytes), $H_2O_2$-induced Btk and PLCγ2 phosphorylation (Ramos cells), or anti-IgM-induced B cell proliferation or CD86 expression on primary B cells (PBMC and splenocytes).

Regulation of Btk activity can also be determined on human, monkey, rat or mouse mast cells following activation FcεR induced degranulation, cytokine production and CD63 induced cell surface expression.

Furthermore, regulation of Btk activity can be determined on CD14+ monocytes differentiated following treatment with M-CSF to osteoclasts and activated with RANKL.

Activity of Btk inhibitors can be investigated in mouse splenocytes following administration in vivo. In a typical experiment mice can be euthanized 3 h following compound administration. Spleens can be extracted from the treated mice for splenocyte isolation. Splenocytes can be plated in 96 well culture plates and stimulated with anti-IgM, without further addition of compounds. Anti-IgM-induced B cell stimulation and inhibition thereof by Btk inhibitors can be measured by B cell proliferation, MIP1β production or CD86 expression on CD19+ splenocyte B cells.

Efficacy of Btk inhibitors can also be investigated in the mouse collagen induced arthritis model using a therapeutic protocol with start of treatment following onset of disease, measuring disease score, X-ray analysis of bone destruction, cartilage breakdown and histology of joints Efficacy of Btk inhibitors on the regulation of activated mast cells can be investigated in vivo using the passive cutaneous anaphylaxis model.

The effect of Btk inhibitors on bone resorption in vivo can be investigated using the rat OVX model. In this model ovariectomized animals develop symptoms of osteoporosis that may be regulated using a Btk inhibitor.

The compounds of Formula I can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The compounds of Formula I may have the ability to crystallize in more than one form, a characteristic known as polymorphism, and it is understood that such polymorphic forms ("polymorphs") are within the scope of Formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The compounds having Formula I or the pharmaceutically acceptable salts or solvates thereof may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

One or more compounds of the invention having Formula I or the pharmaceutically acceptable salts or solvates thereof may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula I (e.g. those labeled with $^3H$ and $^{14}C$) are useful in compound and/or substrate tissue distribution assays. Tritiated (i.e., $^3H$)

and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herinbelow, by substituting an appropriate isotopically labeled reagent for a non-isotopically labeled reagent.

The compounds having Formula I and pharmaceutical compositions thereof can be used to treat or prevent a variety of conditions, diseases or disorders mediated by Bruton's Tyrosine kinase (Btk). Such conditions, diseases or disorders include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g. precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors, myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, vascular spasms, migraine, reperfusion injury, and post-myocardial infarction.

The invention thus provides compounds of Formula (I) and salts, solvates and physiologically functional derivatives thereof for use in therapy, and particularly in the treatment of diseases and conditions mediated by inappropriate Btk activity.

The inappropriate Btk activity referred to herein is any Btk activity that deviates from the normal Btk activity expected in a particular mammalian subject. Inappropriate Btk activity may take the form of, for instance, an abnormal increase in activity, or an aberration in the timing and or control of Btk activity. Such inappropriate activity may result then, for example, from overexpression or mutation of the protein kinase leading to inappropriate or uncontrolled activation.

In a further embodiment, the present invention is directed to methods of regulating, modulating, or inhibiting Btk for the prevention and/or treatment of disorders related to unregulated or inappropriate Btk activity.

In a further embodiment, the present invention provides a method of treatment of a mammal suffering from a disorder mediated by Btk activity, which comprises administering to said mammal an effective amount of a compound of Formula (I) or a pharmaceutically acceptable salt, solvate, or a physiologically functional derivative thereof.

In a further embodiment, the present invention provides for the use of a compound of Formula (I), or a pharmaceutically acceptable salt or solvate thereof, or a physiologically functional derivative thereof, in the preparation of a medicament for the treatment of a disorder mediated by Btk activity.

In a further embodiment said disorder mediated by Btk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fc receptor signaling cascades, including FcεRI and/or FcγRI-mediated degranulation as a therapeutic approach towards the treatment or prevention of diseases characterized by, caused by and/or associated with the release or synthesis of chemical mediators of such Fc receptor signaling cascades or degranulation. In addition, Btk is known to play a critical role in immunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

A further aspect of the invention resides in the use of a compound of Formula I or a pharmaceutically acceptable salt thereof for the manufacture of a medicament to be used for the treatment of Btk-mediated diseases or Btk-mediated conditions.

A further aspect of the invention resides in the use of a compound of Formula I or a pharmaceutically acceptable salt thereof for the manufacture of a medicament to be used for the treatment of chronic B cell disorders in which T cells play a prominent role.

In yet another aspect the invention resides in the use of a compound of Formula I or a pharmaceutically acceptable salt thereof for the manufacture of a medicament to be used for the treatment of Btk-mediated diseases or conditions. These include, but are not limited to, the treatment of B cell lymphomas resulting from chronic active B cell receptor signaling.

Thus, the compounds according to the invention may be used in therapies to treat or prevent diseases Bruton's Tyrosine Kinase (Btk) mediated disorders. Btk mediated disorders or Btk mediated condition as used herein, mean any disease state or other deleterious condition in which B cells, mast cells, myeloid cells or osteoclasts play a central role. These diseases include but are not limited to, immune, autoimmune and inflammatory diseases, allergies, infectious diseases, bone resorption disorders and proliferative diseases.

Immune, autoimmune and inflammatory diseases that may be treated or prevented with the compounds of the present invention include rheumatic diseases (e.g. rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis), glomerulonephritis (with or without nephrotic syndrome), Goodpasture's syndrome, (and associated glomerulonephritis and pulmonary hemorrhage), atherosclerosis, autoimmune hematologic disorders (e.g. hemolytic anemia, aplastic anemia, idiopathic thrombocytopenia, chronic idiopathic thrombocytopenic purpura (ITP), and neutropenia), autoimmune gastritis, and autoimmune inflammatory bowel diseases (e.g. ulcerative colitis and Crohn's disease), irritable bowel syndrome, host versus graft disease, allograft rejection, chronic thyroiditis, Graves' disease, Sjorgren's disease, scleroderma, diabetes (type I and type II), active hepatitis (acute and chronic), pancreatitis, primary billiary cirrhosis, myasthenia gravis, multiple sclerosis, systemic lupus erythematosis, psoriasis, atopic dermatitis, dermatomyositis, contact dermatitis, eczema, skin sunburns, vasculitis (e.g. Behcet's disease), ANCA-associated and other vasculitudes, chronic renal insufficiency, Stevens-Johnson syndrome, inflammatory pain, idiopathic sprue, cachexia, sarcoidosis, Guillain-Barré syndrome, uveitis, conjunctivitis, kerato conjunctivitis, otitis media, periodontal disease, Addison's disease, Parkinson's disease, Alzheimer's disease, diabetes, septic shock, myasthenia gravis, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g. chronic obstructive pulmonary disease) and other inflammatory or obstructive disease on airways.

Allergies that may be treated or prevented include, among others, allergies to foods, food additives, insect poisons, dust mites, pollen, animal materials and contact allergans, type I hypersensitivity allergic asthma, allergic rhinitis, allergic conjunctivitis.

Infectious diseases that may be treated or prevented include, among others, sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

Bone resorption disorders that may be treated or prevented include, among others, osteoporosis, osteoarthritis, traumatic arthritis, gouty arthritis and bone disorders related with multiple myeloma.

Proliferative diseases that may be treated or prevented include, among others, non-Hodgkin lymphoma (in particular the subtypes diffuse large B-cell lymphoma (DLBCL) and mantle cell lymphoma (MCL)), B cell chronic lymphocytic leukemia and acute lymphoblastic leukemia (ALL) with mature B cell, ALL in particular.

In particular the compounds of Formula I or pharmaceutically acceptable salts may be used for the treatment of B cell lymphomas resulting from chronic active B cell receptor signaling.

Included herein are methods of treatment and/or pharmaceutical compositions in which at least one compound of Formula I or a pharmaceutically acceptable salt thereof is administered in combination with at least one other active agent. The other active agent is an anti-inflammatory agent, an immunosuppressant agent, or a chemotherapeutic agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory agent is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant agent, such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., J. Biol. Chem. 1998, 274, 1646-1656).

It has also been discovered that BTK inhibitors are useful as chemosensitizing agents, and, thus, are useful in combination with other chemotherapeutic agents, in particular, drugs that induce apoptosis. Examples of other chemotherapeutic agents that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also been associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. J. Exp. Med. 2005 201(11):1837-1852).

While it is possible that, for use in therapy, a compound of Formula (I), as well as salts, solvates and physiological functional derivatives thereof, may be administered as the raw chemical, it is possible to present the active ingredient as a pharmaceutical composition. Accordingly, the invention further provides a pharmaceutical composition, which comprises a compound of Formula (I) and salts, solvates and physiological functional derivatives thereof, and one or more pharmaceutically acceptable carriers, diluents, or excipients. The compounds of the Formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula (I), or salts, solvates and physiological functional derivatives thereof, with one or more pharmaceutically acceptable carriers, diluents or excipients.

Pharmaceutical compositions of the present invention may be presented in unit dose forms containing a predetermined amount of active ingredient per unit dose. Such a unit may contain, for example, 5 µg to 1 g, preferably 1 mg to 700 mg, more preferably 5 mg to 100 mg of a compound of the Formula (I), depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, sublingual, subcutaneous, local or parenteral (including intravenous and intramuscular) route, and the like, all in unit dosage forms for administration. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, Chronic Obstructive Pulmonary disease (COPD) or Acute Respiratory Distress Syndrome (ARDS).

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula (I) is in a particle-size-reduced form, and more preferably the size-reduced form is obtained or obtainable by micronisation. The preferable particle size of the size-reduced (e.g. micronised) compound or salt or solvate is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula (I) or salt or solvate thereof (preferably in particle-size-reduced form, e.g. in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula (I) or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurized aerosols, nebulizers or insufflators.

For pharmaceutical compositions suitable and/or adapted for intranasal administration, the compound of Formula (I) or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The invention further includes a pharmaceutical composition of a compound of Formula I or pharmaceutically acceptable salts thereof, as hereinbefore described, in combination with packaging material suitable for said composition, said packaging material including instructions for the use of the composition for the use as hereinbefore described.

The following are examples of representative pharmaceutical dosage forms for the compounds of this invention:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |

Water for injection to a total volume of 1 ml

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the particular compound having Formula I, the nature of the formulation, and the route of administration, and will ultimately be at the discretion of the attendant physician or veterinarian. However, an effective amount of a compound of Formula (I) for the treatment of diseases or conditions associated with inappropriate Btk activity, will generally be in the range of 5 µg to 100 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula (I) per se.

In general parenteral administration requires lower dosages than other methods of administration which are more dependent upon absorption. However, a dosage for humans preferably contains 0.0001-25 mg of a compound of Formula I or pharmaceutically acceptable salts thereof per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

The present invention also relates to a pharmaceutical composition comprising a compound of Formula I or pharmaceutically acceptable salt thereof in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition comprising at least one compound of Formula I or pharmaceutically acceptable salts thereof in combination with at least one other therapeutically active agent.

Compounds of the present invention, and their salts and solvates, and physiologically functional derivatives thereof, may be employed alone or in combination with other therapeutic agents for the treatment of Btk mediated diseases and conditions associated with inappropriate Btk activity. Combination therapies according to the present invention thus comprise the administration of at least one compound of Formula (I) or a pharmaceutically acceptable salt or solvate thereof, or a physiologically functional derivative thereof, and the use of at least one other pharmaceutically active agent. The compound(s) of Formula (I) and the other pharmaceutically active agent(s) may be administered together or separately and, when administered separately this may occur simultaneously or sequentially in any order. The amounts of the compound(s) of Formula (I) and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of Formula I may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) nonselective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2), p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for "triple combination" therapy, comprising a compound of Formula (I) or a pharmaceutically acceptable salt thereof together with beta$_2$-adrenoreceptor agonist and an anti-inflammatory corticosteroid. Preferably this combination is for treatment and/or prophylaxis of asthma, COPD or allergic rhinitis. The beta$_2$-adrenoreceptor agonist and/or the anti-inflammatory corticosteroid can be as described above and/or as described in WO 03/030939 A1. Representative examples of such a "triple" combination are a compound of Formula (I) or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol).

For the treatment of cancer a compound of Formula I may be combined with one or more of an anticancer agents. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) antiproliferative agent such asantisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-□α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanaline, 5-amino-1-[[3,5-dichloro-4-(4-chlorobenzoyl)phenyl] methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl)

methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxyl)phenoxy)propoxy)-2-ethyl-chromane-2-carboxylic acid (disclosed in U.S. Ser. No. 60/235,708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AG014699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]-formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of Formula I include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

General Synthesis

The 8-amino-imidazo[1,5-a]pyrazine, 4-amino-imidazo [1,5-f][1,2,4]triazine, 4-amino-pyrazolo[3,4-d]pyrimidine and 4-amino-pyrrolo[1,2-f][1,2,4]triazine derivatives of the present invention can be prepared by methods well known in the art of organic chemistry. See, for example, J. March, 'Advanced Organic Chemistry' 4$^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' 3$^{rd}$ Edition, John Wiley and Sons, 1999. The protective groups are optionally removed at a convenient subsequent stage using methods well known in the art.

The products of the reactions are optionally isolated and purified, if desired, using conventional techniques, but not limited to, filtration, distillation, crystallization, chromatography and the like. Such materials are optionally characterized using conventional means, including physical constants and spectral data.

The 8-amino-imidazo[1,5-a]pyrazine, 4-amino-imidazo[1, 5-f][1,2,4]triazine, 4-amino-pyrazolo[3,4-d]pyrimidine and 4-amino-pyrrolo[1,2-f][1,2,4]triazine derivatives of the present invention can be prepared by methods well known in the art of organic chemistry. See, for example, J. March, 'Advanced Organic Chemistry' 4$^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' 3$^{rd}$ Edition, John Wiley and Sons, 1999. The protective groups are optionally removed at a convenient subsequent stage using methods well known in the art.

The products of the reactions are optionally isolated and purified, if desired, using conventional techniques, but not limited to, filtration, distillation, crystallization, chromatography and the like. Such materials are optionally characterized using conventional means, including physical constants and spectral data.

8-amino-imidazo[1,5-a]pyrazine compounds of formula I, wherein $R_1$-$R_x$ have the previously defined meanings, can be prepared by the general synthetic route shown in scheme I.

Scheme I

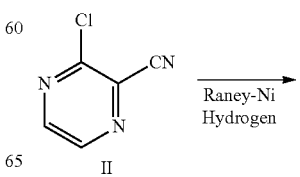

II

-continued

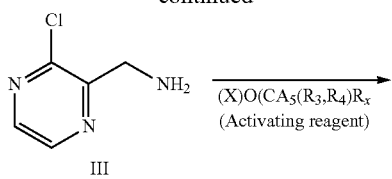

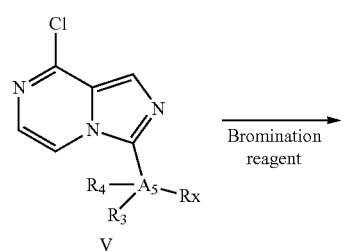

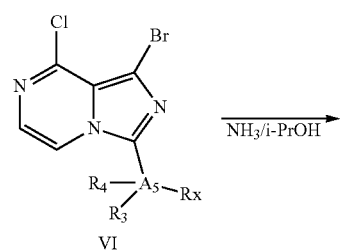

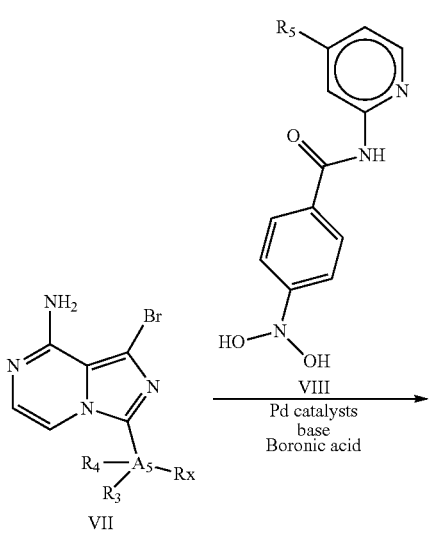

-continued

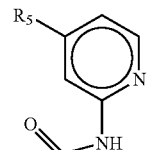

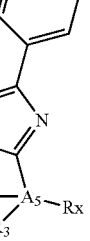

Reduction of 3-chloropyrazine-2-carbonitrile (II) can be accomplished by hydrogenation in the presence of a suitable catalyst system and solvent, for example Raney-Nickel to provide (3-chloropyrazin-2-yl)methanamine (III). This can then be reacted either with an appropriately amine protected amino acid where A5 is equivalent to CH and X is equivalent to OH. The reaction of HO(O)CC($R_3$,$R_4$)$R_x$ can be carried out in a solvent such as DMF, THF or DCM in the presence of a base such as DIPEA, N-methylmorpholine, 4-DMAP or triethylamine and in the presence of a coupling reagent such as PyBOP, TBTU, EDCI or HATU to form N-((3-chloropyrazin-2-yl)methyl)amide (IV). Alternatively, if A5 is equivalent to nitrogen, NH($R_3$,$R_4$)$R_x$ can be activated with trichloromethyl chloroformate or phosgene to introduce COX, where X is equivalent to a leaving group. Subsequent reaction with (3-chloropyrazin-2-yl)methanamine (III) in a suitable solvent like DCM, EtOAc or DMF in the presence of a base such as DiPEA or triethylamine can give compounds of formula IV. Cyclisation chloropyrazine (IV) can be performed using condensation reagents like phosphorousoxychloride under heating conditions to provide the 8-chloroimidazo[1,5-a]pyrazine derivatives V. Subsequent bromination can be accomplished using bromine or N-bromosuccinimide in a suitable solvent like DCM or DMF at appropriate temperature to obtain compounds of formula VI. 8-Aminoimidazo[1,5-a]pyrazine derivatives (VII) can be prepared from compounds VI using ammonia(gas) in isopropanol at elevated temperature in a pressure vessel (>4 atm). Compounds of formula I can be prepared from compounds of formula VII using an appropriate boronic acid or pinacol ester (VIII), in the presence of a suitable palladium catalyst system, for example bis(diphenylphosphino)ferrocene palladium(II)chloride complex or tetrakis(triphenylphosphine)palladium(0) in the presence of an inorganic base like potassium carbonate, cesium carbonate or potassium phosphate in a suitable solvent system like combinations of dioxane and water.

The compounds like COXA$_5$($R_3$,$R_4$)$R_x$ are either commercially available or they can be readily prepared using methods well known to the skilled organic chemist, to introduce protecting groups like benzyloxycarbonyl or tert-butyloxycarbonyl.

Palladium catalysts and conditions to form either the pinacol esters or to couple the boronic acids or pinacol esters with the 1-bromoimidazo[1,5-a]pyrazin-8-amine are well known to the skilled organic chemist—see, for example, Ei-ichi Negishi (Editor), Armin de Meijere (Associate Editor), Handbook of Organopalladium Chemistry for Organic Synthesis, John Wiley and Sons, 2002.

4-Amino-pyrazolo[3,4-d]pyrimidine compounds of formula IX, wherein $R_1$-$R_x$ have the previously defined meanings, can be prepared by the general synthetic route shown in scheme II.

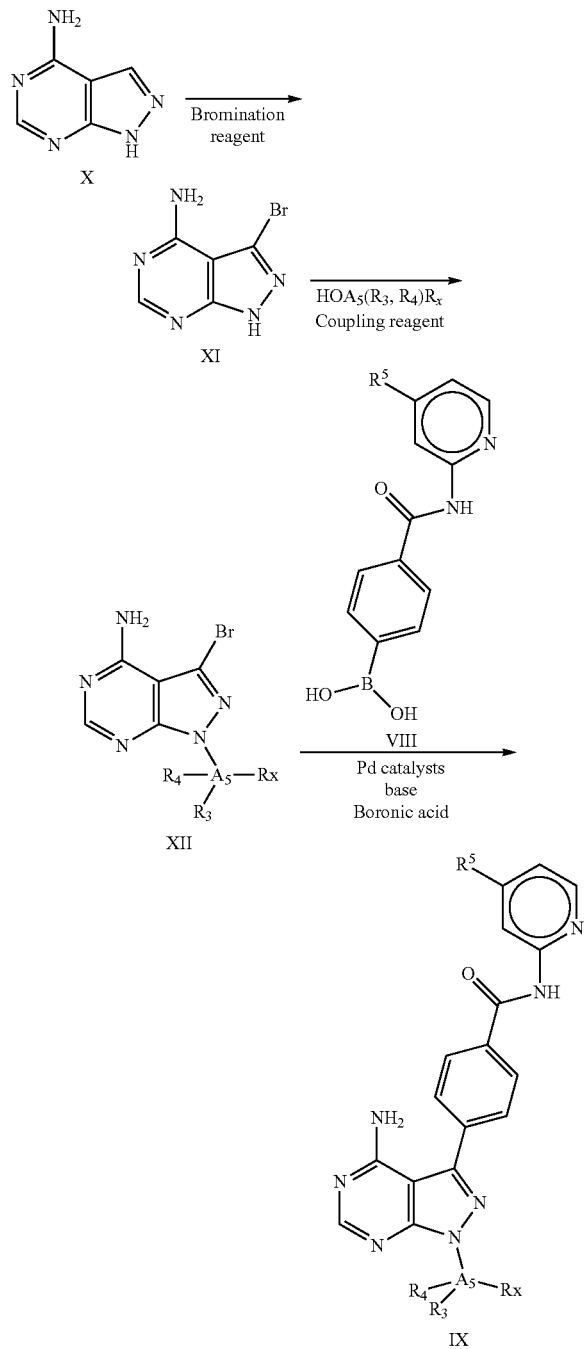

Commercially available starting material 1H-pyrazolo[3,4-d]pyrimidin-4-amine (X) can be converted into the corresponding bromide compound XI with an appropriate bromination reagent such as bromine or N-bromosuccinimide in a suitable solvent like DCM or DMF at appropriate temperature. The reaction of $HOA_5(R_3,R_4)R_x$ can be carried out in a solvent such as DMF, THF or DCM in the presence of a coupling reagent like TPP and DIAD to form 4-amino-3-bromopyrazolo[3,4-d]pyrimidine-1-yl derivatives of formula XII. Compounds of formula IX can be prepared from 3-bromo-4-amino-pyrazolo[3,4-d]pyrimidine-1-yl derivatives XII using an appropriate boronic acid or pinacol ester (VIII), in the presence of a suitable palladium catalyst system, for example bis(diphenylphosphino)ferrocene palladium(II)chloride complex or tetrakis(triphenylphosphine)palladium(0) in the presence of an inorganic base like potassium carbonate, cesium carbonate or potassium phosphate in a suitable solvent system like combinations of dioxane and water.

The present invention also includes within its scope all stereoisomeric forms of the Btk inhibitor compounds according to the present invention resulting, for example, because of configurational or geometrical isomerism. Such stereoisomeric forms are enantiomers, diastereoisomers, cis and trans isomers etc. For example where azepane-2-carboxylic acid is used as amino acid, there exists a mixture of two enantiomers. In the case of the individual stereoisomers of compounds of Formula I or salts or solvates thereof, the present invention includes the aforementioned stereoisomers substantially free, i.e., associated with less than 5%, preferably less than 2% and in particular less than 1% of the other stereoisomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g. synthesis with chiral induction, synthesis starting from chiral intermediates, enantioselective enzymatic conversions, separation of stereoisomers using chromatography on chiral media. Such methods are described in *Chirality in Industry* (edited by A. N. Collins, G. N. Sheldrake and J. Crosby, 1992; John Wiley). Likewise methods for synthesis of geometrical isomers are also well known in the art.

The Btk inhibitor compounds of the present invention, which can be in the form of a free base, may be isolated from the reaction mixture in the form of a pharmaceutically acceptable salt. The pharmaceutically acceptable salts may also be obtained by treating the free base of Formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The Btk inhibitor compounds of the present invention also exist as amorphous forms. Multiple crystalline forms are also possible. All the physical forms are included within the scope of the present invention.

Preparation of solvates is generally known. Thus, for example, M. Caira et al, *J Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

The invention is illustrated by the following examples.

EXAMPLES

The following examples are illustrative embodiments of the invention, not limiting the scope of the invention in any way. Reagents are commercially available or are prepared according to procedures in the literature.

Mass Spectrometry: Electron Spray spectra were recorded on the Applied Biosystems API-165 single quad mass spectrometer in alternating positive and negative ion mode using Flow Injection. The mass range was 120-2000 Da and scanned with a step rate of 0.2 Da. and the capillary voltage was set to 5000 V. $N_2$-gas was used for nebulisation.

LC-MS spectrometer (Waters) Detector: PDA (200-320 nm), Mass detector: ZQ and Eluent: A: acetonitrile with 0.05% trifluoroacetic acid, B: acetonitrile/water=1/9 (v/v) with 0.05% trifluoroacetic acid.
Method LCMS (A)
Column Agilent TC-C18, 50×2.1 mm, 5 μm
   A: $H_2O$ (0.1% TFA)
Mobile Phase B:$CH_3CN$ (0.05% TFA)
   Stop Time:4.5 min

| Gradient | |
| --- | --- |
| Time (min) | B % |
| 0 | 1 |
| 0.4 | 1 |
| 3.4 | 90 |
| 3.9 | 100 |
| 3.91 | 1 |

Sample Injection
volume 2 μl
Flow Rate 0.8 ml/min
Wavelength 220 nm
Oven Tem. 50° C.
MS polarity ESI POS
Method B: LC-MS
Column Agilent TC-C18, 50×2.1 mm, 5 μm
   A: $H_2O$ (0.1% TFA)
Mobile Phase B:MeCN (0.05% TFA)
   Stop Time:4.5 min

| Gradient | |
| --- | --- |
| Time (min) | B % |
| 0 | 1 |
| 0.4 | 1 |
| 3.4 | 90 |
| 3.9 | 100 |
| 3.91 | 1 |

Sample Injection
volume 2 μl
Flow Rate 0.8 ml/min
Wavelength 220 nm
Oven Temp. 50° C.
MS polarity ESI POS Method C:
Sample Info: Easy-Access Method: '1-Short_TFA_Pos'
Method Info: B222 Column Agilent SBC (3.0×50 mm, 1.8μ); Flow 1.0 mL/min;
solvent A: $H_2O$-0.1% TFA;
solvent B: MeCN-0.1% TFA;
GRADIENT TABLE: 0 min:10% B, 0.3 min:10% B, 1.5 min:95% B, 2.70 min:95% B, 2.76 min:10% B
stop time 3.60 min, PostTime 0.70 min.
Method D:
Sample Info: Easy-Access Method: '1_Fast'
   Method Info: A330 Column Agilent Zorbax SB-C18 (2.1×30 mm, 3.5μ); Flow 2.0 mL/min;
solvent A: $H_2O$-0.1% TFA;
solvent B: MeCN-0.1% TFA;
GRADIENT TABLE: 0.01 min:10% B, 1.01 min:95% B, 1.37 min:95% B, 1.38 min:10% B,
stop time 1.7 min, PostTime=OFF
Method E:
Mobile Phase: 0.1% TFA in MeCN and 0.1% TFA in Water
Column: Xterra 2.1×20 mm 3.5 μm IS or SunFire
Flow rate=1.5 mL/min
Injection Volume=5 μL
Column Heater=50° C.
Run time 4 min
Flow rate=1.5 mL/min
Injection Volume=5 μL

| Gradient: | | |
| --- | --- | --- |
| Time | % A | % B |
| 0.00 | 95 | 5 |
| 3.00 | 5 | 95 |
| 3.25 | 2 | 98 |
| 3.26 | 95 | 5 |

Method F:
Mobile Phase: A: 0.1% TFA in MeCN and B: 0.1% TFA in Water
Column: Xterra 2.1×20 mm 3.5 μm IS or SunFire
Flow rate=1.5 mL/min
Injection Volume=5 μL
Column Heater=50° C.
Run time 2 min
Flow rate=1.5 mL/min
Injection Volume=5 μL

| Gradient: | | |
| --- | --- | --- |
| Time | % A | % B |
| 0.00 | 95 | 5 |
| .75 | 5 | 95 |
| 1.25 | 2 | 98 |
| 1.26 | 95 | 5 |

Method G:
Acquity UPLC BEH-C18, 1.7 μm, 2.1×50 mm
1 mL/min flow
5%-100% MeCN in 1.4 min
0.1% $NH_3$
Preparative HPLC was conducted on a column (50×10 mm ID, 5 μm, Xterra Prep MS C18) at a flow rate of 5 ml/min, injection volume 500 μl, at room temperature and UV Detection at 210 nm.

The following abbreviations are used throughout the application with respect to chemical terminology:
HATU O-(7-Azabenzotriazol-1-yl)-1,1,3,3-tetramethyluroniumhexafluoro phosphate
Cbz Benzyloxycarbonyl
DMF N,N-Dimethylformamide
DCM Dichloromethane
EtOAc Ethyl acetate
DIPEA N,N-Diisopropylethylamine
THF Tetrahydrofuran
EtOH Ethanol
EDCI.HCl 1-(3-Dimethylaminopropyl)-3-ethylcarbodiimide. hydrochloride
4-DMAP 4-Dimethylamino pyridine
PyBOP O-Benzotriazole-1-yl-oxy-trispyrrolidinophosphonium hexafluorophosphate
TBTU O-Benzotriazol-1-yl-N,N,N',N'-tetramethyluronium tetrafluoroborate
HBr Hydrogen bromide
HCl Hydrogen chloride
HOAc Acetic acid
POCl₃ Phosphorous oxychloride
HPLC High Pressure Liquid Chromatography
UPLC Ultra Performance Liquid Chromatography
LiHMDS Lithium hexamethyldisilazide
MeOH Methanol
DCM Dichloromethane
n-BuLi n-Butyllithium
CO₂ Carbondioxide
NaHCO₃ Sodiumbicarbonate
K₃PO₄ Potassium phosphate
P(Cy)₃ Tricyclohexylphosphine
Pd(OAc)₂ Palladium(II) acetate
Na₂SO₄ Sodium sulfate
Na₂CO₃ Sodium carbonate
DAST Diethylaminosulfur trifluoride
CS₂CO₃ Cesium carbonate
Et₂O Diethylether
Na₂S₂O₃ Sodium thiosulfate
Na₂S₂O₄ Sodium hydrosulfite
NaCNBH₃ Sodium cyanoborohydride
NH₄Cl Ammonium chloride
MgSO₄ Magnesium sulfate
LiOH Lithium hydroxide
IPA Isopropylamine
TFA Trifluoro acetic acid
Cbz-Cl Benzylchloroformate
PE Petroleum ether
EA Ethyl acetate
NaHMDS Sodium hexamethyldisilazide
10% Pd/C 10% Palladium on carbon
TEA Triethyl amine
CDI 1,1'-Carbonyl diimidazole
DMI 1,3-Dimethyl-2-imidazolidinone
NBS N-Bromosuccinimide
i-PrOH 2-Propanol
K₂CO₃ Potassium carbonate
Pd(dppf)Cl₂ 1,1'-Bis(diphenylphosphino)ferrocene palladium (II) chloride, complex with dichloromethane
Et₃N Triethylamine
2-BuOH 2-Butanol
LCMS Liquid Chromatography/Mass Spectrometry
MeCN Acetonitril
NH₃ Ammonia
CD₃I Trideuteromethyl iodide
CD₃OD Tetradeuteromethanol
CH₃I Iodomethane
CBr₄ Carbon tetrabromide
Tris-HCl Tris(hydroxymethyl)aminomethane.hydrochloride
MgCl₂ Magnesium chloride
NaN₃ Sodium azide
DTT Dithiothreitol
DMSO Dimethyl sulfoxide
IMAP Immobilized Metal Ion Affinity-Based Fluorescence Polarization
ATP Adenosine triphosphate
MnCl₂ Manganese(II)chloride
DMA Dimethylacetamide
IPA Isopropyl alcohol
TPP triphenylphosphine
DIAD Diisopropyl azodicarboxylate
DMB 2,4-dimethoxybenzyl
DCE Dichloroethane
DEAD Diethyl azodicarboxylate
ACN Acetonitrile
RT (rt) Room Temperature
Aq Aqueous
EtOH Ethanol
MPLC Medium Pressure Liquid Chromoatography
Xantphos 4,5-Bis(diphenylphosphino)-9,9-dimethylxanthene
X-phos 2-Dicyclohexylphosphino-2',4',6'-triisopropylbiphenyl
TFA trifluoroacetic acid Intermediate 1

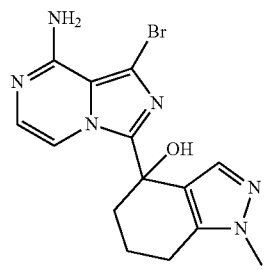 [SMILES: Cn1ncc2c1CCCC2(O)c1nc(Br)c2c(N)nccn12]

1-bromo-3-(1-methyl-4,5,6,7-tetrahydro-1H-indazol-4-yl)imidazo[1,5-a]pyrazin-8-amine (a)
2-((dimethylamino)methylene)cyclohexane-1,3-dione A mixture of cyclohexane-1,3-dione (33.6 g, 300 mmol) in DMF-DMA (120 ml) was heated to 100° C. and stirred for 1 h under nitrogen protection. The volatiles were concentrated under reduced pressure. The red solid (55 g crude) was used in the next step directly.

(b) 1-methyl-6,7-dihydro-1H-indazol-4(5H)-one

To a solution of 2-((dimethylamino)methylene)cyclohexane-1,3-dione (55 g crude, 300 mmol) in t-BuOH (400 ml) was added methylhydrazine solution (35 g, 40% aqueous solution, 304 mmol) and AcOH (20 ml) at room temperature. The resulting mixture was heated to reflux for 3 h under nitrogen protection. After cooling, the mixture was concentrated in vacuo and the residue was purified by column chromatograph on silica gel (petroleum ether/ethyl acetate=1/1 v/v %) to give 1-methyl-6,7-dihydro-1H-indazol-4(5H)-one (20 g, two steps: 44%). MS-ESI (m/z): 151 (M+1)⁺ (Acq Method: 0-60AB_2 min; Rt: 0.90 min)

(c) 4-(8-chloroimidazo[1,5-a]pyrazin-3-yl)-1-methyl-4,5,6,7-tetrahydro-1H-indazol-4-ol To a solution of 1-methyl-6,7-dihydro-1H-indazol-4(5H)-one (770 mg, 5 mmol) in anhydrous THF (10 ml) was added n-BuLi (2.5M, 2 ml, 5 mmol) dropwise at −78° C. under nitrogen protection. After the addition was completed, the mixture was stirred at −78° C. for further 15 min, then another solution of 8-chloroimidazo[1,5-a]pyrazine (710 mg, 4.75 mmol) in anhydrous THF (5 ml) was added slowly. The reaction mixture was allowed to warm to room temperature and for 1 h. The mixture was diluted with water and extracted with ethyl acetate three times. The combined organic layers were dried over Na₂SO₄ and concentrated in vacuo. The residue was purified by column chromatography on silica gel (MeOH/DCM=1/50 to 1/15 v/v %) to give 4-(8-chloroimidazo pyrazin-3-yl)-1-methyl-4,5,6,7-tetrahydro-1H-indazol-4-ol (1 g, 70%). MS-ESI (m/z): 304 (M+1)⁺ (Acq Method: 0-60AB_2 min; Rt: 1.07 min)

(d) 4-(1-bromo-8-chloroimidazo[1,5-a]pyrazin-3-yl)-1-methyl-4,5,6,7-tetrahydro-1H-indazol-4-ol To a solution of 4-(8-chloroimidazo[1,5-a]pyrazin-3-yl)-1-methyl-4,5,6,7-tetrahydro-1H-indazol-4-ol (1 g, 3.3 mmol) in DMF (8 ml) was added NBS (584 mg, 3.3 mmol) portionwise at 0° C. After the addition was complete, the reaction mixture was stirred at 0° C. for 30 minutes. The mixture was diluted with water and extracted with ethyl acetate three times. The combined organic layers were washed with brine, dried over Na₂SO₄ and concentrated in vacuo. The residue was purified by preparative TLC to give 4-(1-bromo-8-chloroimidazo[1,5-a]pyrazin-3-yl)-1-methyl-4,5,6,7-tetrahydro-1H-indazol-4-ol (860 mg, 68%). MS-ESI (m/z): 382 (M+1)⁺ (Acq Method: 10-80AB_2 min; Rt: 1.01 min)

(e) 4-(8-amino-1-bromoimidazo[1,5-a]pyrazin-3-yl)-1-methyl-4,5,6,7-tetrahydro-1H-indazol-4-ol A mixture of 4-(1-bromo-8-chloroimidazo[1,5-a]pyrazin-3-yl)-1-methyl-4,5,6,7-tetrahydro-1H-indazol-4-ol (860 mg, 2.26 mmol) in NH₃/i-PrOH (2N, 25 ml) was added in a sealed tube, and then stirred at 120° C. overnight. After cooling to room temperature, the mixture was filtered and the filtrate was evaporated under reduce pressure. The residue was re-dissolved in DCM, washed with water and brine, dried over MgSO₄ and concentrated in vacuo to give 4-(8-amino-1-bromoimidazo[1,5-a]pyrazin-3-yl)-1-methyl-4,5,6,7-tetrahydro-1H-indazol-4-ol (720 mg, 88%). MS-ESI (m/z): 363 (M+1)⁺ (Acq Method: 0-60AB_2 min; Rt: 0.98 min)

Intermediate 2

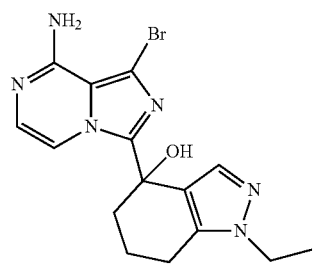 [SMILES: CCn1ncc2c1CCCC2(O)c1nc(Br)c2c(N)nccn12]

4-(8-amino-1-bromoimidazo[1,5-a]pyrazin-3-yl)-1-ethyl-4,5,6,7-tetrahydro-1H-indazol-4-ol This intermediate was prepared, in an analogues manner as described in Intermediate 1 from step b to e, starting from ethylhydrazine, to afford the title compound.

Intermediate 3

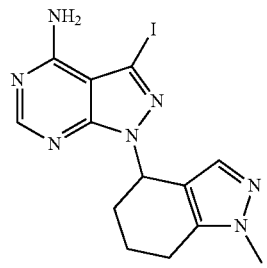 [SMILES: Cn1ncc2c1CCCC2n1nc(I)c2c(N)ncnc21]

3-iodo-1-(1-methyl-4,5,6,7-tetrahydro-1H-indazol-4-yl)-1H-pyrazolo[3,4-d]pyrimidin-4-amine (a) 1-methyl-4,5,6,7-tetrahydro-1H-indazol-4-ol To a solution of 1-methyl-6,7-dihydro-1H-indazol-4(5H)-one (1 g, 6.7 mmol) in EtOH (20 mL) was added NaBH₄ (1.2 g, 33.3 mmol) in portions. The resulting mixture was stirred at room temperature for 30 min. The solvent was removed under reduced pressure to afford the crude 1-methyl-4,5,6,7-tetrahydro-1H-indazol-4-ol (700 mg, 68.8%), which was used in the next step directly. MS-ESI (m/z): 153 (M+1)⁺ (Acq Method: 10-80AB_2 min_220 &254.1 cm; Rt: 0.17 min)

(b) 3-iodo-1-(1-methyl-4,5,6,7-tetrahydro-1H-indazol-4-yl)-1H-pyrazolo[3,4-d]pyrimidin-4-amine To a solution of 1-methyl-4,5,6,7-tetrahydro-1H-indazol-4-ol (400 mg, 2.63 mmol) and 3-iodo-1H-pyrazolo[3,4-d]pyrimidin-4-amine (684 mg, 2.63 mmol) and Ph₃P (1.03 g, 3.94 mmol) in THF (40 mL) was added DIAD (798 mg, 3.94 mmol) dropwise at 0° C. After the addition was completed, the mixture was allowed to warm to room temperature and stirred for 3 hours. The mixture was extracted with EA, the combined the organic layers were washed with brine and dried over anhydrous Na₂SO₄. The volatiles were concentrated in vacuo and the residue was purified by silica gel chromatography (DCM/methanol=40/1 v/v %) to give 3-iodo-1-(1-methyl-4,5,6,7-tetrahydro-1H-indazol-4-yl)-1H-pyrazolo[3,4-d]pyrimidin-4-amine (80 mg, 8%). MS-ESI (m/z): 396 (M+1)⁺ (Acq Method: 10-80AB_2 min_220 &254.1 cm; Rt: 0.82 min)

Intermediate 4

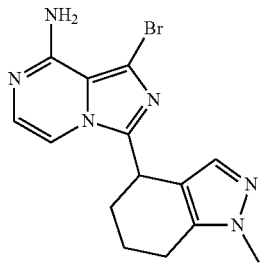 [SMILES: Cn1ncc2c1CCCC2c1nc(Br)c2c(N)nccn12]

1-bromo-3-(1-methyl-4,5,6,7-tetrahydro-1H-indazol-4-yl)imidazo[1,5-a]pyrazin-8-amine (a) 1-methyl-6,7-dihydro-1H-indazol-4-yl trifluoromethanesulfonate To a solution of 1-methyl-6,7-dihydro-1H-indazol-4(5H)-one (10 g, 66.6 mmol) and PhNTf$_2$ (26 g, 66.6 mmol) in anhydrous THF (250 mL) was added KHMDS (0.5 M in THF, 140 mL, 70 mmol) dropwise at −78° C. After the addition was completed, the mixture was stirred at room temperature for 16 hours. The solvent was removed and the residue was purified by column chromatography on silica gel (PE/THF=5/1 v/v %) to afford 1-methyl-6,7-dihydro-1H-indazol-4-yl trifluoromethanesulfonate (12 g, 64%).

MS-ESI (m/z): 283 (M+1)$^+$ (Acq Method: 10-80AB_2 min_220 &254.1 cm; Rt: 1.05 min)

(b) methyl 1-methyl-6,7-dihydro-1H-indazole-4-carboxylate

A solution of 1-methyl-6,7-dihydro-1H-indazol-4-yl trifluoromethanesulfonate (12 g, 42.5 mmol) and Pd(OAc)$_2$ (1 g, 4.25 mmol) in DMF (150 mL) and MeOH (15 mL) was carried out carbonylation at 70° C. for 4 hours under carbon monoxide atmosphere. The volatiles were removed under reduced pressure and the residue was purified by column chromatography on silica gel (PE/THF=5/1 v/v %) to afford methyl 1-methyl-6,7-dihydro-1H-indazole-4-carboxylate (7.5 g, 91%).

MS-ESI (m/z): 193 (M+1)$^+$ (Acq Method: 10-80AB_2 min_220 &254.1 cm; Rt: 0.84 min)

(c) methyl 1-methyl-4,5,6,7-tetrahydro-1H-indazole-4-carboxylate

To a solution of 1-methyl-6,7-dihydro-1H-indazole-4-carboxylate (7.5 g, 38.7 mmol) and NiCl$_2$ (4.9 g, 38.7 mmol) in MeOH (250 mL) was added NaBH$_4$ (14 g, 387 mmol) in portions at 0° C. The resulting mixture was stirred at room temperature for further 1 hour. The solvent was removed and the residue was purified by column chromatography on silica gel (PE/THF=5/1 v/v %) to afford methyl 1-methyl-4,5,6,7-tetrahydro-1H-indazole-4-carboxylate (7 g, 94%).

MS-ESI (m/z): 195 (M+1)$^+$ (Acq Method: 10-80AB_2 min_220 &254.1 cm; Rt: 0.89 min)

(d) 1-methyl-4,5,6,7-tetrahydro-1H-indazole-4-carboxylic acid

To a solution of 1-methyl-4,5,6,7-tetrahydro-1H-indazole-4-carboxylate (7 g, 36 mmol) in methanol (100 mL), THF (50 mL) and H$_2$O (50 mL) was added LiOH (2.5 g, 108 mmol). The resulting mixture was stirred at room temperature for 2 hours. The reaction mixture was acidified with 1N HCl solution to pH=5-6, and extracted with EA three times. The combined organic layers were washed with brine, dried over Na$_2$SO$_4$. The solvent was concentrated to give 1-methyl-4,5,6,7-tetrahydro-1H-indazole-4-carboxylic acid (6 g, 94%), which was used in the next step directly.

(e) N-((3-chloropyrazin-2-yl)methyl)-1-methyl-4,5,6,7-tetrahydro-1H-indazole-4-carboxamide To a solution of 1-methyl-4,5,6,7-tetrahydro-1H-indazole-4-carboxylic acid (6 g, 33 mmol) and (3-chloropyrazin-2-yl)methanamine hydrochloride (6 g, 33 mmol) in 200 mL of DCM was added TEA (9 g, 88 mmol) dropwise. The resulting mixture was stirred at room temperature for 5 mins, and then HATU (12.5 g, 33 mmol) was added to the solution in portions at 0° C. The mixture was stirred at room temperature for 2 hours. Water was added, the DCM layers was separated, and washed with brine, dried over Na$_2$SO$_4$. The solvent was removed and the residue was purified by column chromatography on silica gel (PE/THF=5/1 v/v %) to afford N-((3-chloropyrazin-2-yl)methyl)-1-methyl-4,5,6,7-tetrahydro-1H-indazole-4-carboxamide (1.5 g, 15%).

MS-ESI (m/z): 306 (M+1)$^+$ (Acq Method: 10-80AB_2 min_220 &254.1 cm; Rt: 0.93 min)

(f) 8-chloro-3-(1-methyl-4,5,6,7-tetrahydro-1H-indazol-4-yl)imidazo[1,5-a]pyrazine To a solution of N-((3-chloropyrazin-2-yl)methyl)-1-methyl-4,5,6,7-tetrahydro-1H-indazole-4-carboxamide (1.5 g, 4.9 mmol) in MeCN (50 mL) was added POCl$_3$ (1.2 g, 7.9 mmol) dropwise and DMF (0.1 mL). The mixture was stirred at 60° C. for 4 hours. After cooling, the mixture was poured into ice-water and extracted with EA three times. The EA layer was washed with brine and dried over Na$_2$SO$_4$. The solvent was removed and the residue was purified by column chromatography on silica gel (DCM/methanol=40/1 v/v %) to afford 8-chloro-3-(1-methyl-4,5,6,7-tetrahydro-1H-indazol-4-yl)imidazo[1,5-a]pyrazine (1.0 g, 70.4%). MS-ESI (m/z): 288 (M+1)$^+$ (Acq Method: 10-80AB_2 min_220 &254.1 cm; Rt: 0.85 min)

(g) 1-bromo-8-chloro-3-(1-methyl-4,5,6,7-tetrahydro-1H-indazol-4-yl)imidazo[1,5-a]pyrazine To a solution of 8-chloro-3-(1-methyl-4,5,6,7-tetrahydro-1H-indazol-4-yl)imidazo[1,5-a]pyrazine (1.0 g, 3.5 mmol) in DMF (20 mL) was added NBS (600 mg, 3.4 mmol) dropwise in DMF (20 mL) at 0° C. The mixture was stirred about 10 min under this condition, and then was poured into ice-water. The solid was filtered and dried under high vacuum to give 1-bromo-8-chloro-3-(1-methyl-4,5,6,7-tetrahydro-1H-indazol-4-yl)imidazo[1,5-a]pyrazine (200 mg, 15.6%). MS-ESI (m/z): 368 (M+1)$^+$ (Acq Method: 10-80AB_2 min_220 &254.1 cm; Rt: 1.04 min)

(h) 1-bromo-3-(1-methyl-4,5,6,7-tetrahydro-1H-indazol-4-yl)imidazo[1,5-a]pyrazin-8-amine A solution of 1-bromo-8-chloro-3-(1-methyl-4,5,6,7-tetrahydro-1H-indazol-4-yl)imidazo[1,5-a]pyrazine (200 mg, 0.5 mmol) in NH$_3$/i-PrOH (2N, 5 mL) in a sealed tube was stirred at room temperature for 16 hours. The solvent was removed to give 1-bromo-8-chloro-3-(1-methyl-4,5,6,7-tetrahydro-1H-indazol-4-yl)imidazo[1,5-a]pyrazine (150 mg, 87%). MS-ESI (m/z): 349 (M+1)+ (Acq Method: 10-80AB_2 min_220 &254.1 cm; Rt: 0.97 min)

Intermediate 5E1 and 5E2

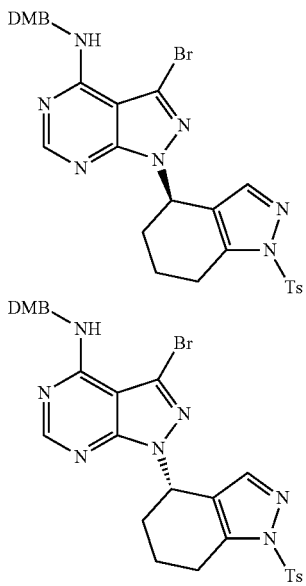

(a) 1-tosyl-6,7-dihydro-1H-indazol-4(5H)-one

A solution of 2-((dimethylamino)methylene)cyclohexane-1,3-dione (55 g, 0.329 mol), 2-tosylhydrazine (61.3 g, 0.329 mol) and AcOH (33 mL) in EtOH (540 mL) was heated for 4 h at 70° C. Removed the solvent under reduced pressure and the residue was recrystallized using PE/EA=5/1 to give 1-tosyl-6,7-dihydro-1H-indazol-4(5H)-one (49 g, yield 51.3%) as a white solid.

$^1$H-NMR (400 MHz, CD$_3$OD) δ ppm 7.99 (s, 1H), 7.92~7.94 (d, J=8.4 Hz, 2H), 7.37~7.39 (d, J=8.4 Hz, 2H), 3.26~3.29 (t, J=6.4 Hz, 2H), 2.48~2.51 (t, J=6.8 Hz, 2H), 2.45 (s, 3H), 2.17~2.23 (m, 2H).

(b) 1-tosyl-4,5,6,7-tetrahydro-1H-indazol-4-ol

To a solution of 1-tosyl-6,7-dihydro-1H-indazol-4(5H)-one (5 g, 17.22 mmol) in EtOH/THF (30 mL/30 mL)) was added NaBH$_4$ (1.3 g, 34.44 mmol) under ice-bath. The mixture was stirred for 1 h at this temperature and quenched with aqueous NH$_4$Cl solution. Removed the solvent under reduced pressure and extracted with DCM and the combined organic layer was washed with water, brine and dried over anhydrous Na$_2$SO$_4$. The organic layer was concentrated in vacuo and the residue 1-tosyl-4,5,6,7-tetrahydro-1H-indazol-4-ol (4.94 g, yield 98.2%) was used directly to next step. MS-ESI (m/z): 293 (M+1)+ (Acq Method: 10-80AB_2 min; Rt: 1.01 min)

(c) 3-bromo-N-(2,4-d methoxybenzyl)-1-(1-tosyl-4,5,6,7-tetrahydro-1H-indazol-4-yl)-1H-pyrazolo[3,4-d]pyrimidin-4-amine A solution of 1-tosyl-4,5,6,7-tetrahydro-1H-indazol-4-ol (4.05 g, 11.13 mmol), 3-bromo-N-(2,4-dimethoxybenzyl)-1H-pyrazolo[3,4-d]pyrimidin-4-amine (3.9 g, 13.35 mmol) and PPh$_3$ (4.38 g, 16.70 mmol) in dry THF (110 mL) at 0° C. was added dropwise DIAD (3.37 g, 16.70 mmol) over a period of 5 minutes under a nitrogen atmosphere, then the mixture was stirred at room temperature for 4 hours. Removed the solvent under reduced pressure and then extracted with DCM, the combined organic layer was washed with water, brine and dried over anhydrous Na$_2$SO$_4$. The organic layer was concentrated in vacuo and the residue was purified by preparative HPLC separation to afford 3-bromo-N-(2,4-dimethoxybenzyl)-1-(1-tosyl-4,5,6,7-tetrahydro-1H-indazol-4-yl)-1H-pyrazolo[3,4-d]pyrimidin-4-amine (2.3 g, yield 32.4%). MS-ESI (m/z): 640 (M+2)+ (Acq Method: 10-80AB_2 min; Rt: 1.357 min)

(d) (R)-3-bromo-N-(2,4-dimethoxybenzyl)-1-(1-tosyl-4,5,6,7-tetrahydro-1H-indazol-4-yl)-1H-pyrazolo[3,4-d]pyrimidin-4-amine and (S)-3-bromo-N-(2,4-dimethoxybenzyl)-1-(1-tosyl-4,5,6,7-tetrahydro-1H-indazol-4-yl)-1H-pyrazolo[3,4-d]pyrimidin-4-amine The two enantiomers (R)-3-bromo-N-(2,4-dimethoxybenzyl)-1-(1-tosyl-4,5,6,7-tetrahydro-1H-indazol-4-yl)-1H-pyrazolo[3,4-d]pyrimidin-4-amine (1.1 g) (E1) and (S)-3-bromo-N-(2,4-dimethoxy benzyl)-1-(1-tosyl-4,5,6,7-tetrahydro-1H-indazol-4-yl)-1H-pyrazolo[3,4-d]pyrimidin-4-amine (E2) (1.0 g) was obtained after SFC separation from intermediate 28 (2.3 g).

Acq Method:
Column: Chiralpak AS-H 150*4.6 mm I.D., 5 um Mobile phase: methanol (0.05% DEA) in CO$_2$ from 5% to 40% Flow rate: 3 mL/min Wavelength: 220 nm Intermediate 6

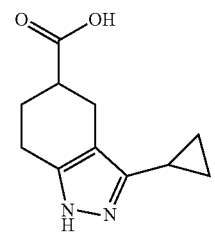 [SMILES: O=C(O)C1CCc2[nH]nc(C3CC3)c2C1]

3-cyclopropyl-4,5,6,7-tetrahydro-1H-indazole-5-carboxylic acid (a) methyl 4-morpholinocyclohex-3-enecarboxylic acid The solution of methyl 4-oxocyclohexanecarboxylic acid (172.0 g, 1.01 mol), morpholine (97.0 g, 1.11 mol) and p-toluenesulfonic acid (200 mg) in toluene (500 mL) was stirred 18 h at reflux. The reaction mixture was concentrated in vacuum to give 235 g methyl 4-morpholinocyclohex-3-enecarboxylic acid. The compound was used in the next reaction without further purification.

(b) methyl 3-(cyclopropanecarbonyl)-4-oxocyclohexanecarboxylic acid

The crude compound methyl 4-morpholinocyclohex-3-enecarboxylic acid (134.0 g, 0.56 mol) was dissolved in anhydrous DCM (1.0 L) in the presence of Et₃N (89.0 g, 0.88 mol). Cyclopropanecarbonyl chloride (73.0 g, 0.70 mol) was added dropwise at 0° C. The reaction mixture was stirred 18 h at rt. The reaction mixture was acidified with 5% HCl solution to pH=3 at 10° C. After stirring for 30 min at room temperature, the organic layer was separated. The aqueous layer was extracted by EtOAc (3×70 mL). The organic phase was washed with brine, dried (Na₂SO₄) and concentrated. The crude product was purified using gel chromatography (Petroleumether/EtOAc 6/1) to give 36.0 g methyl 3-(cyclopropanecarbonyl)-4-oxocyclohexanecarboxylic acid (27% yield for 2 steps).

(c) methyl 3-cyclopropyl-4,5,6,7-tetrahydro-1H-indazole-5-carboxylate

To a solution of compound 3-(cyclopropanecarbonyl)-4-oxocyclohexanecarboxylic acid (36.0 g, 0.15 mol) in EtOH (95%, 300 mL) was added hydrazine hydrate (23.0 g, 0.39 mol) at 0° C. The reaction mixture was stirred 18 h at rt. The solvent was concentrated in vacuum to give methyl 3-cyclopropyl-4,5,6,7-tetrahydro-1H-indazole-5-carboxylate (35.0 g). The compound was used in the next reaction without further purification.

(d) 3-cyclopropyl-4,5,6,7-tetrahydro-1H-indazole-5-carboxylic acid

To a solution methyl 3-cyclopropyl-4,5,6,7-tetrahydro-1H-indazole-5-carboxylate (35.0 g) in MeOH (300 mL) was added a solution of LiOH.H₂O (10.8 g, 0.26 mol) in H₂O (200 mL) at 0° C. After stirring 18 h at rt the solvent was removed in vacuum. To the residue water (200 mL) was added and aqueous solution was acidified to pH=4-5 with 10% HCl. The precipitate was collected by filtration to give 3-cyclopropyl-4,5,6,7-tetrahydro-1H-indazole-5-carboxylic acid (25.0 g, 80% yield for 2 steps).

Intermediate 7

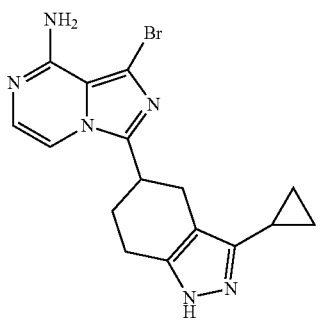 [SMILES: Nc1nccn2c(C3CCc4[nH]nc(C5CC5)c4C3)nc(Br)c12]

1-bromo-3-(3-cyclopropyl-4,5,6,7-tetrahydro-1H-indazol-5-yl)imidazo[1,5-a]pyrazin-8-amine This intermediate was prepared, in an analogues manner as described for intermediate 21, from 3-cyclopropyl-4,5,6,7-tetrahydro-1H-indazole-5-carboxylic acid (Intermediate 24) to obtain the title compound (235 mg, 66.3%).

Intermediate 8

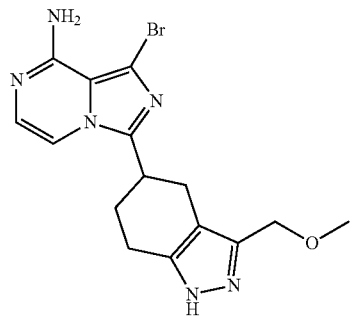 [SMILES: COCc1n[nH]c2c1CC(c1nc(Br)c3c(N)nccn13)CC2]

1-bromo-3-(3-(methoxymethyl)-4,5,6,7-tetrahydro-1H-indazol-5-yl)imidazo[1,5-a]pyrazin-8-amine This intermediate was prepared, in an analogues manner as described for intermediate 24 and 21, from 3-(methoxymethyl)-4,5,6,7-tetrahydro-1H-indazole-5-carboxylic acid to obtain the title compound (140 mg, 44.8%).

Intermediate 9E1 and 9E2

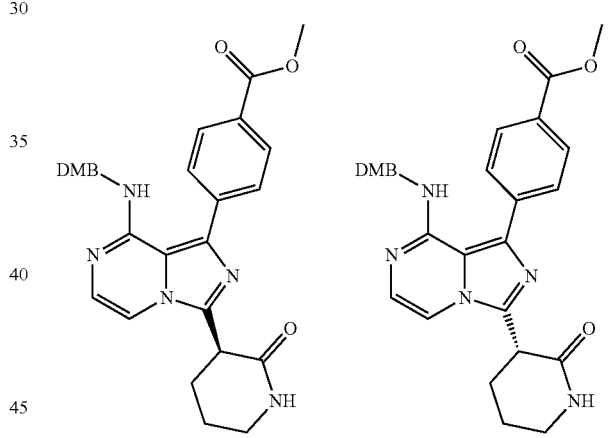

(S)-methyl 4-(8-((2,4-dimethoxybenzyl)amino)-3-(2-oxopiperidin-3-yl)imidazo[1,5-a]pyrazin-1-yl)benzoate and (R)-methyl 4-(8-((2,4-dimethoxybenzyl)amino)-3-(2-oxopiperidin-3-yl)imidazo[1,5-a]pyrazin-1-yl)benzoate

(a) (E)-methyl 4-((benzhydrylimino)methyl)benzoate

To a solution of methyl 4-formylbenzoate (50 g, 305 mmol) in EA (600 mL) was added 1a (56 g, 305 mmol). The mixture was heated to reflux for 4 hrs. After the reaction was completed, the mixture was cooled to RT and filtered, the solid was washed with EA/PE (1/1,v/v, 150 mL) and dried to give (E)-methyl 4-((benzhydrylimino)methyl)benzoate (80 g, yield 80%).

¹H-NMR (400 MHz, CD₃OD) δ ppm 8.64 (s, 1H), 7.94~8.03 (m, 4H), 7.38 (d, J=4.6 Hz, 4H), 7.30 (t, J=8.0 Hz, 4H), 7.20 (t, J=7.2 Hz, 2H), 5.71 (s, 1H), 3.84 (s, 1H).

(b) methyl 4-(amino(3-chloropyrazin-2-yl)methyl)benzoate

To a solution of (E)-methyl 4-((benzhydrylimino)methyl) benzoate (67 g, 204 mmol) in THF (700 mL) was cooled to 0° C. and added dropwise NaHMDS (244 mL, 244 mmol). The mixture was stirred at this temperature for 30 minutes, and added a solution of 2,3-dichloropyrazine (33.2 g, 224 mmol) in THF (40 mL). The reaction mixture was stirred at 0° C. for 20 minutes and RT for 40 minutes. After the reaction was completed, the reaction mixture was extracted with EA and water. The organic layer was treated with 3M HCl (500 mL) for 10 minutes. The phases were separated and the organic layer was extracted with 3M HCl. The aqueous was washed with EA and then alkalified with $Na_2CO_3$ to pH=9. The aqueous solution was extracted with EA and the combined organics were dried and concentrated to give methyl 4-(amino(3-chloropyrazin-2-yl)methyl)benzoate (46 g, yield 81%).

MS-ESI (m/z): 278 $(M+1)^+$ (Acq Method: 10-80AB_2 min; Rt: 0.75 min).

(c) methyl 4-((3-chloropyrazin-2-yl)(2-cyanoacetamido)methyl)benzoate

To a solution of methyl 4-(amino(3-chloropyrazin-2-yl) methyl)benzoate (54 g, 195 mmol) in THF (500 mL) was added 2-cyanoacetic acid (16.6 g, 195 mmol) and TEA (39.4 g, 390 mmol). The mixture was added HATU (74.1 g, 195 mmol) at 0-5° C., and stirred at room temperature for 1 h. The reaction mixture was extracted with EA and water, the organic layer was dried and concentrated. The residue was purified by column chromatography on silica gel eluted with PE:EA=2:1 to give methyl 4-((3-chloropyrazin-2-yl)(2-cyanoacetamido)methyl)benzoate (67 g, yield 100%).

MS-ESI (m/z): 345 $(M+1)^+$ (Acq Method: 10-80AB_2 min; Rt: 0.93 min).

(d) methyl 4-(8-chloro-3-(cyanomethyl)imidazo[1,5-a]pyrazin-1-yl)benzoate

To a solution of methyl 4-((3-chloropyrazin-2-yl)(2-cyanoacetamido)methyl)benzoate (84 g, 244 mmol) in DCM (1.6 L) was added $Tf_2O$ (150 mL). The mixture was stirred at RT overnight. After the reaction was completed, the solvent was evaporated. The residue was alkalified with $NaHCO_3$ solution and extracted with EA. The organic layer was dried and concentrated, the residue was purified by column chromatography on silica gel eluted with PE:DCM:EA=1:1:1 to give methyl 4-(8-chloro-3-(cyanomethyl)imidazo[1,5-a]pyrazin-1-yl) benzoate (42 g, yield 53%).

MS-ESI (m/z): 327 $(M+1)^+$ (Acq Method: 10-80AB_2 min; Rt: 1.01 min).

(e) methyl 4-(3-(cyanomethyl)-8-((2,4-dimethoxybenzyl)amino)imidazo[1,5-a]pyrazin-1-yl) benzoate In 1 L seal tube, added a solution of 4-(8-chloro-3-(cyanomethyl)imidazo[1,5-a]pyrazin-1-yl) benzoate (41 g, 126 mmol) in dioxane (500 mL), (2,4-dimethoxyphenyl) methanamine (42 g, 252 mmol) and DIEA (48.7 g, 377 mmol). The mixture was stirred at 155° C. for 5 hrs. The reaction mixture was concentrated and the residue was purified by column chromatography on silica gel eluted with PE:EA:DCM=2:1:1 to give methyl 4-(3-(cyanomethyl)-8-((2,4-dimethoxybenzyl)amino)imidazo[1,5-a]pyrazin-1-yl) benzoate (32 g, yield 56%).

$^1$H-NMR (400 MHz, $CD_3OD$) δ ppm 8.0 (d, J=8.4 Hz, 2H), 7.71 (d, J=8.0 Hz, 2H), 7.58 (d, J=5.2 Hz, 1H), 7.23 (d, J=4.8 Hz, 1H), 7.09 (d, J=8.4 Hz, 1H), 6.40~6.50 (m, 2H), 5.89 (t, J=5.6 Hz, 1H), 4.57 (s, 2H), 4.46 (d, J=5.2 Hz, 2H), 3.86 (s, 3H), 3.69 (s, 3H), 3.60 (s, 3H).

(f) methyl 4-(8-((2,4-dimethoxybenzyl)amino)-3-(2-methoxy-2-oxoethyl)imidazo[1,5-a]pyrazin-1-yl) benzoate To a solution of methyl 4-(3-(cyanomethyl)-8-((2,4-dimethoxybenzyl)amino)imidazo[1,5-a]pyrazin-1-yl)benzoate (12 g, 26.2 mmol) in HCl/MeOH (150 mL) was stirred at RT for 2 hrs. After the reaction was completed, the mixture was neutralized with aq $NaHCO_3$ and extracted with EA and water. The organic layer was dried and concentrated. The residue was purified by column chromatography on silica gel eluted with PE:EA:DCM=2:1:1 to give methyl 4-(8-((2,4-dimethoxybenzyl)amino)-3-(2-methoxy-2-oxoethyl)imidazo[1,5-a]pyrazin-1-yl)benzoate (11 g, yield 86%).

$^1$H-NMR (400 MHz, $CD_3OD$) δ ppm 7.99 (d, J=8.4 Hz, 2H), 7.70 (d, J=8.0 Hz, 2H), 7.57 (d, J=4.8 Hz, 1H), 7.15 (d, J=4.8 Hz, 1H), 7.11 (d, J=8.4 Hz, 1H), 6.47 (d, J=2.0 Hz, 1H), 6.39~6.42 (m, 1H), 5.85 (t, J=5.6 Hz, 1H), 4.46 (d, J=5.2 Hz, 2H), 4.22 (s, 2H), 3.86 (s, 3H), 3.69 (s, 3H), 3.61 (s, 3H), 3.57 (s, 3H).

(g) methyl 4-(3-(4-cyano-1-methoxy-1-oxobutan-2-yl)-8-((2,4-dimethoxybenzyl)amino)imidazo[1,5-a] pyrazin-1-yl)benzoate To a solution of methyl 4-(8-((2,4-dimethoxybenzyl) amino)-3-(2-methoxy-2-oxoethyl) imidazo[1,5-a]pyrazin-1-yl)benzoate (11.4 g, 23.3 mmol) in THF (100 mL) was added acrylonitrile (1.4 g, 25.6 mmol) and t-BuOK (2.3 mL, 1M in THF). The mixture was stirred at RT for 2 hrs. The reaction was complete detected by TLC (PE/EtOAc 1:1). The mixture was extracted with EA and water, the organic layer was dried and concentrated, the residue was purified by column chromatography on silica gel eluted with PE:EA:DCM=2:1:1 to give methyl 4-(3-(4-cyano-1-methoxy-1-oxobutan-2-yl)-8-((2,4-dimethoxybenzyl)amino)imidazo[1,5-a]pyrazin-1-yl)benzoate (12 g, yield 94%).

$^1$H-NMR (400 MHz, $CD_3OD$) δ ppm 8.01 (d, J=8.0 Hz, 2H), 7.59 (d, J=8.0 Hz, 2H), 7.10~7.20 (m, 3H), 6.30~6.35 (m, 2H), 5.62 (t, J=5.2 Hz, 1H), 4.53 (d, J=5.6 Hz, 2H), 4.13 (t, J=6.4 Hz, 1H), 3.90 (s, 3H), 3.71 (s, 3H), 3.64 (s, 3H), 3.45 (s, 3H), 2.42~2.62 (m, 4H).

(h) methyl 4-(8-((2,4-dimethoxybenzyl)amino)-3-(2-oxopiperidin-3-yl)imidazo[1,5-a]pyrazin-1-yl)benzoate To a solution of methyl 4-(3-(4-cyano-1-methoxy-1-oxobutan-2-yl)-8-((2,4-dimethoxybenzyl)amino)imidazo[1,5-a]pyrazin-1-yl)benzoate (12 g, 22.1 mmol) in EtOH (350 mL) was added Ra—Ni (24 g) under $N_2$. The suspension was degassed under vacuum and purged with H2 several times. The mixture was stirred under H2 (50 psi) at 75° C. for 7 hours. The reaction was complete detected by LCMS. The suspension was filtered through a pad of Celite and the pad was washed with EtOH (20 mL×3). The combined filtrates were concentrated. The residue was purified by column chromatography on silica gel eluted with DCM:MeOH=30:1 to give methyl 4-(8-((2,4-dimethoxybenzyl) amino)-3-(2-oxopiperidin-3-yl)imidazo[1,5-a]pyrazin-1-yl) benzoate (4.6 g, yield 40%).

¹H-NMR (400 MHz, CD₃OD) δ ppm 7.99 (d, J=8.4 Hz, 2H), 7.76 (s, 1H), 7.69 (d, J=8.8 Hz, 2H), 7.62 (d, J=5.6 Hz, 1H), 7.11 (d, J=7.2 Hz, 2H), 6.39~6.48 (m, 2H), 5.78 (t, J=5.2 Hz, 1H), 4.46 (d, J=5.6 Hz, 2H), 4.20~4.24 (m, 1H), 3.87 (s, 3H), 3.70 (s, 3H), 3.57 (s, 3H), 3.22~3.29 (m, 2H), 1.73~2.32 (m, 4H).

(I) (S)-methyl 4-(8-((2,4-dimethoxybenzylamino)-3-(2-oxopiperidin-3-yl)imidazo[1,5-a]pyrazin-1-yl) benzoate and (R)-methyl 4-(8-((2,4-dimethoxybenzyl)amino)-3-(2-oxopiperidin-3-yl) imidazo[1,5-a] pyrazin-1-yl)benzoate The above product was separated by SFC to give the title compounds.
Acq Method:
Column: Chiralpak AS-H 250×4.6 mm I.D., 5 um Mobile phase: 40% methanol (0.05% DEA) in CO2 Flow rate: 2.35 mL/min Wavelength: 220 nm Intermediate 10

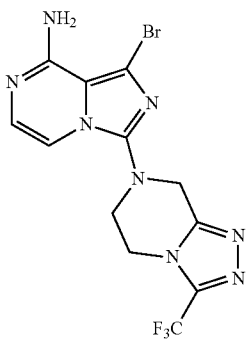 [SMILES: Nc1nccn2c(N3CCn4c(nnc4C(F)(F)F)C3)nc(Br)c12]

1-Bromo-3-(3-(trifluoromethyl)-5,6-dihydro-[1,2,4] triazolo[4,3-a]pyrazin-7(8H)-yl)imidazo[1,5-a] pyrazin-8-amine (a) N-((3-chloropyrazin-2-yl)methyl)-3-(trifluoromethyl)-5,6-dihydro-[1,2,4]triazolo[4,3-a]pyrazine-7 (8H)-carboxamide A stirred solution of trichloromethyl carbonochloridate (1.038 g, 5.25 mmol) in tetrahydrofuran (10 mL) was cooled to 0° C. and a solution of 3-(trifluoromethyl)-5,6,7,8-tetrahydro-[1,2,4]triazolo[4,3-a]pyrazine hydrochloride (1 g, 4.37 mmol, J. Med. Chem., 2005, 141) and N-ethyl-N-isopropylpropan-2-amine (1.131 g, 8.75 mmol) in tetrahydrofuran (10 mL) was added slowly in 25 minutes. After stirring at 0° C. for one hour the solids were removed by filtration and the filtrate was concentrated in vaccuo (50° C. bath temperature). The residue was added to a solution of (3-chloropyrazin-2-yl)methanamine hydrochloride (0.788 g, 4.37 mmol) and triethylamine (1.018 g, 10.06 mmol) in dichloromethane (20 mL) and the reaction mixture was stirred for three hours. The solids were removed by filtration and the filtrate was concentrated in vacuo. Purification using column chromatography (silica gel; gradient dichloromethane/methanol 100:0 to 95:5) to afford N-((3-chloropyrazin-2-yl)methyl)-3-(trifluoromethyl)-5,6-dihydro-[1,2,4]triazolo[4,3-a]pyrazine-7(8H)-carboxamide (1.56 g, 4.31 mmol, 99% yield). LC-MS: C12H11ClF3N7O: 361. found 362.04[M+H]⁺, RT=0.42 min.

(b) 7-(8-chloroimidazo[1,5-a]pyrazin-3-yl)-3-(trifluoromethyl)-5,6,7,8-tetrahydro-[1,2,4]triazolo[4,3-a]pyrazine To a stirred solution of N-((3-chloropyrazin-2-yl)methyl)-3-(trifluoromethyl)-5,6-dihydro-[1,2,4]triazolo[4,3-a]pyrazine-7(8H)-carboxamide (1.25 g, 3.46 mmol) in Acetonitrile (10 ml) was added pyridine (2.73 g, 34.6 mmol) and finally phosphoryl trichloride (2.65 g, 17.28 mmol). The resulting reaction mixture was then stirred at room temperature for 15 hours overnight. The reaction was quenched by slowly addition of NaHCO₃ and extracted with ethyl acetate (3×). The organic layer was dried by MgSO₄, filtered and concentrated. The residue was purified by MPLC (24 g silica gel, 20 to 60% ethyl acetate in hexaes, 18 CV) to afford white solid product 7-(8-chloroimidazo[1,5-a]pyrazin-3-yl)-3-(trifluoromethyl)-5,6,7,8-tetrahydro-[1,2,4]triazolo[4,3-a]pyrazine (550 mg, 1.600 mmol, 46.3% yield). LC-MS: C12H9ClF3N7,343. found 344.11 [M+H]+, RT=1.22 min.

(c) 7-(1-bromo-8-chloroimidazo[1,5-a]pyrazin-3-yl)-3-(trifluoromethyl)-5,6,7,8-tetrahydro-[1,2,4]triazolo[4,3-a]pyrazine To a 100 ml one neck round bottom flask was charged with 7-(8-chloroimidazo[1,5-a]pyrazin-3-yl)-3-(trifluoromethyl)-5,6,7,8-tetrahydro-[1,2,4]triazolo[4,3-a]pyrazine (540 mg, 1.571 mmol) along with DMF (5 ml). The mixture was stirred and 1-bromopyrrolidine-2,5-dione (308 mg, 1.728 mmol) was added in on batch. The resulting reaction mixture was then stirred at room temperature for 18 hrs overnight. The mixture was diluted with ethyl acetate and washed with NaHCO₃ (sat), water, dried over MgSO₄, filtered and concentrated. The residue was purified by MPLC (24 g silica gel, 50% to 100% ethyl acetate in hexanes, 18 CV) to afford light color solid product 7-(1-bromo-8-chloroimidazo[1,5-a]pyrazin-3-yl)-3-(trifluoromethyl)-5,6,7,8-tetrahydro-[1,2,4]triazolo[4,3-a]pyrazine (595 mg, 1.408 mmol, 90% yield). LC-MS: C12H8BrClF3N7, 421. found 422.02 [M+H]⁺, RT=1.30 min.

(d) 1-bromo-3-(3-(trifluoromethyl)-5,6-dihydro-[1,2,4]triazolo[4,3-a]pyrazin-7(8H)-yl)imidazo[1,5-a] pyrazin-8-amine To a 75 ml sealed vessel was charged with 7-(1-bromo-8-chloroimidazo[1,5-a]pyrazin-3-yl)-3-(trifluoromethyl)-5,6,7,8-tetrahydro-[1,2,4]triazolo[4,3-a]pyrazine (595 mg, 1.408 mmol) along with ammonia in IPA (2N, 0.704 ml, 1.408 mmol). The vessel was sealed with screw cap and heated in an oil bath of 120° C. for 18 hrs overnight. LC-MS showed complete conversion of starting material to product. The mixture was then cooled to room temperature, solid (gel) precipitated and was filtered, washed with IPA and dried to afford 1-bromo-3-(3-(trifluoromethyl)-5,6-dihydro-[1,2,4]triazolo[4,3-a]pyrazin-7(8H)-yl)imidazo[1,5-a] pyrazin-8-amine (250 mg). The filtrate was concentrated and the residue was purified by MPLC (12 g silica gel, 0 to 10% methanol in methylenechloride, 28 CV) to afford another batch of product. Totally 1-bromo-3-(3-(trifluoromethyl)-5, 6-dihydro-[1,2,4]triazolo[4,3-a]pyrazin- 7(8H)-yl)imidazo

[1,5-a]pyrazin-8-amine (386 mg, 0.957 mmol, 68.0% yield) was obtained. LC-MS: C12H10BrF3N8,402. found 403.08 [M+H]+, RT=1.09 min.

Intermediate 11

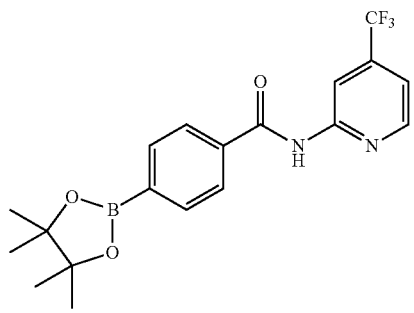 [SMILES: CC1(C)OB(c2ccc(C(=O)Nc3cc(C(F)(F)F)ccn3)cc2)OC1(C)C]

4-(4,4,5,5-tetramethyl-1,3,2-dioxaborolan-2-yl)-N-(4-(trifluoromethyl)pyridin-2-yl)benzamide To the stirred solution of 2-amino-4-(trifluoromethyl)pyridine (10.79 g, 66.6 mmol) and 4-dimethylaminopyridine (7.39 g, 60.5 mmol) in Acetonitrile (125.00 ml) was added a solution of 4-(4,4,5,5-tetramethyl-1,3,2-dioxaborolan-2-yl)benzoyl chloride (16.12 g, 60.50 mmol) in Acetonitrile (75.00 ml) dropwise at room temperature. The solution turned into suspension after about half an hour and was stirred at r. t. overnight. The reaction mixture was concentrated and partitioned between 250 ml 0.2 N HCl and 250 ml CH$_2$Cl$_2$. The organic phase was separated and washed with 2×250 ml 0.2N HCl. The organic phase was dried over MgSO$_4$ and evaporated to dryness. The crude was purified on RediSep 220 g silica cartridge and eluted with 1 lt Hexane, 4 lt 10% EtOAc/Hexane, 4 lt 20% EtOAc/Hexane gave white solid product 4-(4,4,5,5-tetramethyl-1,3,2-dioxaborolan-2-yl)-N-(4-(trifluoromethyl)pyridin-2-yl)benzamide. $^1$HNMR (CD$_3$Cl, 500 MHz, δ): 8.83 (1H, br), 8.71 (1H, s), 8.45 (1H, d), 7.93 (4H, m), 7.30 (1H, d), 1.38 (12H, s).

Intermediate 12

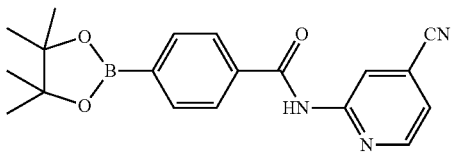 [SMILES: CC1(C)OB(c2ccc(C(=O)Nc3cc(C#N)ccn3)cc2)OC1(C)C]

N-(4-Cyanopyridin-2-yl)-4-(4,4,5,5-tetramethyl-1,3,2-dioxaborolan-2-yl)benzamide This compound was prepared, in an analogous manner as described in Intermediate 11, starting from 2-aminoisonicotinonitrile, to afford the title compound (1.3 g, 99%).

Example 1

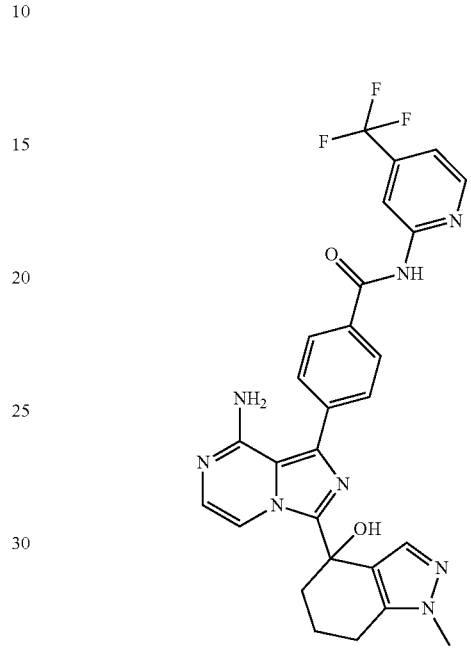

4-(8-amino-3-(4-hydroxy-1-methyl-4,5,6,7-tetrahydro-1H-indazol-4-yl)imidazo[1,5-a]pyrazin-1-yl)-N-(4-(trifluoromethyl)pyridin-2-yl)benzamide The reaction mixture of 4-(8-amino-1-bromoimidazo[1,5-a]pyrazin-3-yl)-1-methyl-4,5,6,7-tetrahydro-1H-indazol-4-ol (580 mg, 1.6 mmol), 4-(4,4,5,5-tetramethyl-1,3,2-dioxaborolan-2-yl)-N-(4-(trifluoromethyl)pyridin-2-yl)benzamide (2 mmol), Pd(dppf)Cl$_2$ (80 mg) and K$_2$CO$_3$ (830 mg, 6 mmol) in a mixed solvent of dioxane (15 mL) and H$_2$O (2 mL) was stirred at 110° C. for 1.5 hrs under N$_2$ protection. After cooling, the resulting mixture was filtered and the filtrate was evaporated under reduce pressure to dryness. The residue was purified by preparative TLC to afford 4-(8-amino-3-(4-hydroxy-1-methyl-4,5,6,7-tetrahydro-1H-indazol-4-yl)imidazo[1,5-a]pyrazin-1-yl)-N-(4-(trifluoromethyl)pyridin-2-yl)benzamide.

$^1$H NMR (CD$_3$OD 400 MHz): δ 8.60 (s, 1H), 8.58 (d, J=5.2 Hz, 1H), 8.16 (d, J=5.6 Hz, 1H), 8.10 (d, J=8.4 Hz, 2H), 7.77 (d, J=8.4 Hz, 2H), 7.41 (d, J=4.4 Hz, 1H), 7.36 (s, 1H), 7.02 (d, J=5.2 Hz, 1H), 3.75 (s, 3H), 2.61-2.79 (m, 2H), 2.35-2.41 (m, 1H), 2.16-2.22 (m, 2H), 1.94-1.99 (m, 1H).

Example 2 and 3

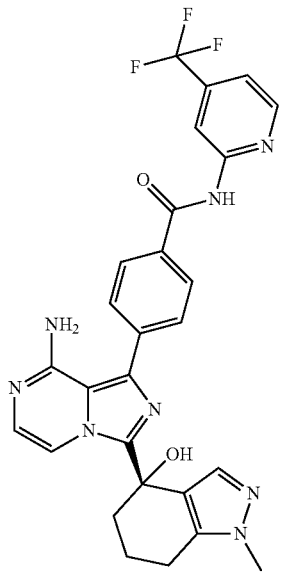

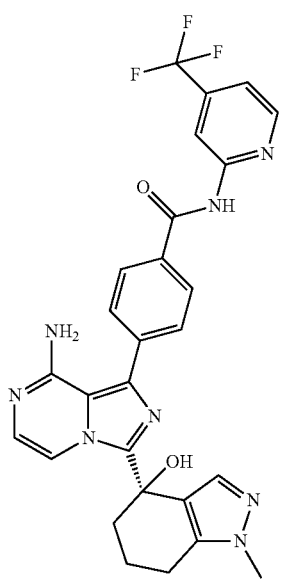 [SMILES: Cn1ncc2c1CCCC2(O)c1nc(-c2ccc(C(=O)Nc3cc(C(F)(F)F)ccn3)cc2)c2c(N)nccn12]

(S)-4-(8-amino-3-(4-hydroxy-1-methyl-4,5,6,7-tetrahydro-1H-indazol-4-yl)imidazo[1,5-a]pyrazin-1-yl)-N-(4-(trifluoromethyl)pyridin-2-yl)benzamide and (R)-4-(8-amino-3-(4-hydroxy-1-methyl-4,5,6,7-tetrahydro-1H-indazol-4-yl)imidazo[1,5-a]pyrazin-1-yl)-N-(4-(trifluoromethyl)pyridin-2-yl)benzamide After separation by SFC, the title two enantiomers were obtained.

Acq method:

Column: Chiralcel OD-3 50*4.6 mm I.D., 3 um Mobile phase: methanol (0.05% DEA) in CO$_2$ from 5% to 40% Flow rate: 4 mL/min Wavelength: 220 nm.

Example 4

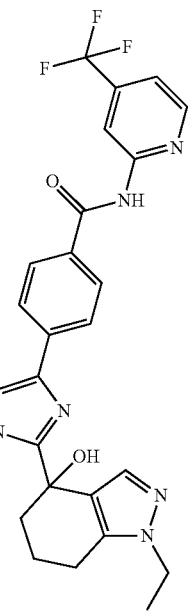

4-(8-amino-3-(1-ethyl-4-hydroxy-4,5,6,7-tetrahydro-1H-indazol-4-yl)imidazo[1,5-a]pyrazin-1-yl)-N-(4-(trifluoromethyl)pyridin-2-yl)benzamide This compound was prepared, in an analogues manner as described in 4-(8-amino-3-(4-hydroxy-1-methyl-4,5,6,7-tetrahydro-1H-indazol-4-yl)imidazo pyrazin-1-yl)-N-(4-(trifluoromethyl)pyridin-2-yl)benzamide, starting from intermediate 22, to afford the title compound.

$^1$H NMR (CD$_3$OD 400 MHz): δ 8.60 (s, 1H), 8.58 (d, J=5.2 Hz, 1H), 8.16 (d, J=5.6 Hz, 1H), 8.09 (d, J=8.4 Hz, 2H), 7.76 (d, J=8.4 Hz, 2H), 7.46-7.57 (m, 2H), 7.39-7.40 (m, 2H), 7.02 (d, J=5.2 Hz, 1H), 4.09 (q, J=7.2 Hz, 2H), 2.62-3.57 (m, 2H), 2.36-2.42 (m, 1H), 2.16-2.24 (m, 2H), 1.97-1.99 (m, 1H), 1.38 (t, J=7.2 Hz, 3H).

Example 5

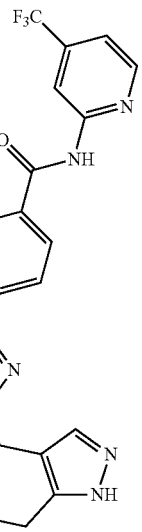

(R)-4-(4-amino-1-(4,5,6,7-tetrahydro-1H-indazol-4-yl)-1H-pyrazolo[3,4-d]pyrimidin-3-yl)-N-(4-(trifluoromethyl)pyridin-2-yl)benzamide (a) (R)-4-(4-((2,4-dimethoxybenzyl)amino)-1-(1-tosyl-4,5,6,7-tetrahydro-1H-indazol-4-yl)-1H-pyrazolo[3,4-d]pyrimidin-3-yl)-N-(4-(trifluoromethyl)pyridin-2-yl)benzamide The mixture of (R)-3-bromo-N-(2,4-dimethoxybenzyl)-1-(1-tosyl-4,5,6,7-tetrahydro-1H-indazol-4-yl)-1H-pyrazolo[3,4-d]pyrimidin-4-amine (80 mg, 0.125 mmol), 4-(4,4,5,5-tetramethyl-1,3,2-dioxaborolan-2-yl)-N-(4-(trifluoromethyl)pyridin-2-yl)benzamide (59 mg, 0.150 mmol), Pd(PPh$_3$)$_2$Cl$_2$ (9.2 mg, 0.0125 mmol) and K$_2$CO$_3$ (43 mg, 0.313 mmol) in dioxane/H$_2$O (3 mL/0.3 mL) was stirred for 2 h at 90° C. under nitrogen atmosphere. Then the mixture was added water and extracted with DCM. The combined organic layer was washed with water, brine and dried over anhydrous Na$_2$SO$_4$. Concentrated in vacuo and the residue was purified with silica gel chromatography with PE/EA=1/1 to give (R)-4-(4-((2,4-dimethoxybenzyl)amino)-1-(1-tosyl-4,5,6,7-tetrahydro-1H-indazol-4-yl)-1H-pyrazolo[3,4-d]pyrimidin-3-yl)-N-(4-(trifluoromethyl)pyridin-2-yl)benzamide (90 mg, yield 87.2%) as yellow solid.

MS-ESI (m/z): 824 (M+1)$^+$ (Acq Method: 10-80AB_2 min; Rt: 1.39 min)

(b) (R)-4-(4-amino-1-(4,5,6,7-tetrahydro-1H-indazol-4-yl)-1H-pyrazolo[3,4-d]pyrimidin-3-yl)-N-(4-(trifluoromethyl)pyridin-2-yl)benzamide A solution of (R)-4-(4-((2,4-dimethoxybenzyl)amino)-1-(1-tosyl-4,5,6,7-tetrahydro-1H-indazol-4-yl)-1H-pyrazolo[3,4-d]pyrimidin-3-yl)-N-(4-(trifluoromethyl)pyridin-2-yl)benzamide (90 mg, 0.109 mmol) in TFA (3 mL) was stirred for 3 h at 100° C. Removed the solvent and purified by preparative HPLC to give the title compound (30 mg, yield 52.8%).

$^1$H-NMR (400 MHz, CD$_3$OD) δ ppm 8.45~8.60 (m, 3H), 8.07~8.16 (m, 2H), 7.64~7.84 (m, 3H), 7.37~7.43 (m, 1H), 6.26 (s, 1H), 2.83~2.89 (m, 2H), 2.35 (m, 3H), 2.03 (m, 1H). MS-ESI (m/z): 520 (M+1)$^+$.

Example 6

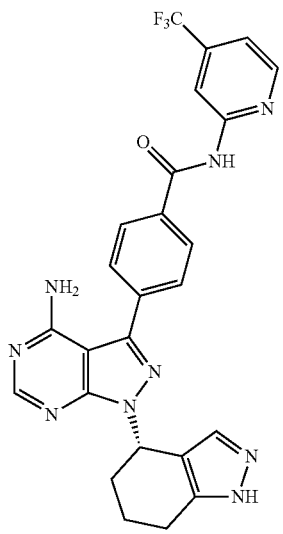 [SMILES: Nc1ncnc2c1c(-c1ccc(C(=O)Nc3cc(C(F)(F)F)ccn3)cc1)nn2[C@H]1CCCc2[nH]ncc21]

(S)-4-(4-amino-1-(4,5,6,7-tetrahydro-1H-indazol-4-yl)-1H-pyrazolo[3,4-d]pyrimidin-3-yl)-N-(4-(trifluoromethyl)pyridin-2-yl)benzamide Same procedure afford (S)-4-(4-amino-1-(4,5,6,7-tetrahydro-1H-indazol-4-yl)-1H-pyrazolo[3,4-d]pyrimidin-3-yl)-N-(4-(trifluoromethyl)pyridin-2-yl)benzamide from (S)-3-bromo-N-(2,4-di methoxybenzyl)-1-(1-tosyl-4,5,6,7-tetrahydro-1H-indazol-4-yl)-1H-pyrazolo[3,4-d]pyrimidin-4-amine.

Example 7 and 8

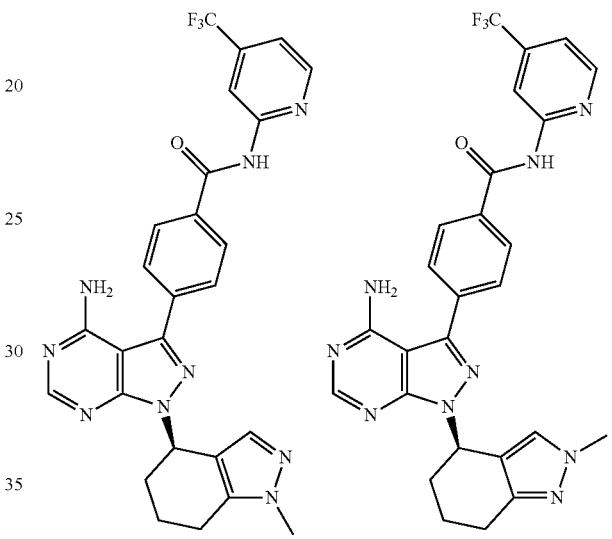

(R)-4-(4-amino-1-(1-methyl-4,5,6,7-tetrahydro-1H-indazol-4-yl)-1H-pyrazolo[3,4-d]pyrimidin-3-yl)-N-(4-(trifluoromethyl)pyridin-2-yl)benzamide and (R)-4-(4-amino-1-(2-methyl-4,5,6,7-tetrahydro-2H-indazol-4-yl)-1H-pyrazolo[3,4-d]pyrimidin-3-yl)-N-(4-(trifluoromethyl)pyridin-2-yl)benzamide (a) (R)-3-bromo-N-(2,4-dimethoxybenzyl)-1-(4,5,6,7-tetrahydro-1H-indazol-4-yl)-1H-pyrazolo[3,4-d]pyrimidin-4-amine To a solution of (R)-3-bromo-N-(2,4-dimethoxybenzyl)-1-(1-tosyl-4,5,6,7-tetrahydro-1H-indazol-4-yl)-1H-pyrazolo[3,4-d]pyrimidin-4-amine (400 mg, 0.626 mmol) in THF (6.3 mL) was added 1N LiOH.H$_2$O (105 mg, 2.504 mmol), then the mixture was stirred for 8 h at 60° C. Removed the solvent under reduced pressure and extracted with DCM and the combined organic layer was washed with water, brine and dried over anhydrous Na$_2$SO$_4$. The organic layer was concentrated in vacuo and the residue (R)-3-bromo-N-(2,4-dimethoxybenzyl)-1-(4,5,6,7-tetrahydro-1H-indazol-4-yl)-1H-pyrazolo[3,4-d]pyrimidin-4-amine (280 mg, yield 92.3%) was used directly to next step.

MS-ESI (m/z): 484 (M+1)$^+$, (Acq Method: 10-80AB_2 min; Rt: 1.07 min)

(b) mixture of (R)-3-bromo-N-(2,4-dimethoxybenzyl)-1-(1-methyl-4,5,6,7-tetrahydro-1H-indazol-4-yl)-1H-pyrazolo[3,4-d]pyrimidin-4-amine and (R)-3-bromo-N-(2,4-dimethoxybenzyl)-1-(2-methyl-4,5,6,7-tetrahydro-2H-indazol-4-yl)-1H-pyrazolo[3,4-d]pyrimidin-4-amine A solution of (R)-3-bromo-N-(2,4-dimethoxybenzyl)-1-(4,5,6,7-tetrahydro-1H-indazol-4-yl)-1H-pyrazolo[3,4-d]pyrimidin-4-amine (100 mg, 0.206 mmol), Cs$_2$CO$_3$ (134 mg, 0.412 mmol) and CH$_3$I (38 mg, 0.268 mmol) in DMF (2.1 mL)) was stirred for 15 minutes at 70° C. under microwave. Removed the solvent under reduced pressure and extracted with DCM and the combined organic layer was washed with water, brine and dried over anhydrous Na$_2$SO$_4$. The organic layer was concentrated in vacuo and the residue was purified by silica gel column chromatography (PE/EA=1/1) to afford the title mixture.

MS-ESI (m/z): 498 (M+1)$^+$, (Acq Method: 10-80AB_2 min; Rt: 1.17 min)

(c) mixture of (R)-4-(4-(2,4-dimethoxybenzyl)amino)-1-(1-methyl-4,5,6,7-tetrahydro-1H-indazol-4-yl)-1H-pyrazolo[3,4-d]pyrimidin-3-yl)-N-(4-(trifluoromethyl)pyridin-2-yl)benzamide and (R)-4-(4-((2,4-dimethoxybenzyl)amino)-1-(2-methyl-4,5,6,7-tetrahydro-2H-indazol-4-yl)-1H-pyrazolo[3,4-d]pyrimidin-3-yl)-N-(4-(trifluoromethyl)pyridin-2-yl)benzamide The above mixture (140 mg, 0.281 mmol), 4-(4,4,5,5-tetramethyl-1,3,2-dioxaborolan-2-yl)-N-(4-(trifluoromethyl)pyridin-2-yl)benzamide (132 mg, 0.337 mmol), Pd(PPh$_3$)$_2$Cl$_2$ (21 mg, 0.0281 mmol) and K$_2$CO$_3$ (97 mg, 0.70 mmol) in dioxane/H$_2$O (5 mL/0.5 mL) was stirred for 2 h at 90° C. under nitrogen atmosphere. Then the mixture was added water and extracted with DCM. The combined organic layer was washed with water, brine and dried over anhydrous Na$_2$SO$_4$. Concentrated in vacuo and the residue was purified with silica gel chromatography with PE/EA=1/1 to give the title mixture (100 mg, yield 72.9%) as yellow solid.

MS-ESI (m/z): 684 (M+1)$^+$ (Acq Method: 10-80AB_2 min; Rt: 1.248 min)

(d) (R)-4-(4-amino-1-(1-methyl-4,5,6,7-tetrahydro-1H-indazol-4-yl)-1H-pyrazolo[3,4-d]pyrimidin-3-N-(4-trifluoromethyl)pyridin-2-yl)benzamide and (R)-4-(4-amino-1-(2-methyl-4,5,6,7-tetrahydro-2H-indazol-4-yl)-1H-pyrazolo[3,4-d]pyrimidin-3-yl)-N-(4-(trifluoromethyl)pyridin-2-yl)benzamide The above mixture (100 mg, 0.146 mmol) in TFA (3 mL) was stirred for 4 h at 80° C. Removed the solvent and separated by SFC to afford (R)-4-(4-amino-1-(1-methyl-4,5,6,7-tetrahydro-1H-indazol-4-yl)-1H-pyrazolo[3,4-d]pyrimidin-3-yl)-N-(4-(trifluoromethyl)pyridin-2-yl) benzamide.

$^1$H NMR (400 MHz, CD$_3$OD) δ ppm 8.58~8.60 (d, J=8.4 Hz, 2H), 8.30 (s, 1H), 8.11~8.13 (d, J=8.0 Hz, 2H), 7.80~7.82 (d, J=8.4 Hz, 2H), 7.41~7.42 (d, J=4.4 Hz, 1H), 7.17 (s, 1H), 6.10~6.13 (t, J=4.8 Hz, 1H), 3.75 (s, 3H), 2.74~2.79 (m, 2H), 2.26~2.37 (m, 3H), 1.93~1.97 (m, 1H).

MS-ESI (m/z): 534 (M+1)$^+$.

and (R)-4-(4-amino-1-(2-methyl-4,5,6,7-tetrahydro-2H-indazol-4-yl)-1H-pyrazolo[3,4-d]pyrimidin-3-yl)-N-(4-(trifluoromethyl)pyridin-2-yl)benzamide $^1$H NMR (400 MHz, CD$_3$OD) δ ppm 8.58~8.61 (d, J=8.4 Hz, 2H), 8.30 (s, 1H), 8.11~8.13 (d, J=8.0 Hz, 2H), 7.80~7.82 (d, J=8.4 Hz, 2H), 7.41~7.42 (d, J=4.4 Hz, 1H), 7.17 (s, 1H), 6.10~6.13 (t, J=4.8 Hz, 1H), 3.75 (s, 3H), 2.74~2.79 (m, 2H), 2.26~2.37 (m, 3H), 1.93~1.97 (m, 1H).

MS-ESI (m/z): 534 (M+1)$^+$.

Acq Method:

Column: Chiralpak AS-H 150*4.6 mm I.D., 5 um Mobile phase: ethanol (0.05% DEA) in CO2 from 5% to 40% Flow rate: 3 mL/min Wavelength: 220 nm.

Example 9 and 10

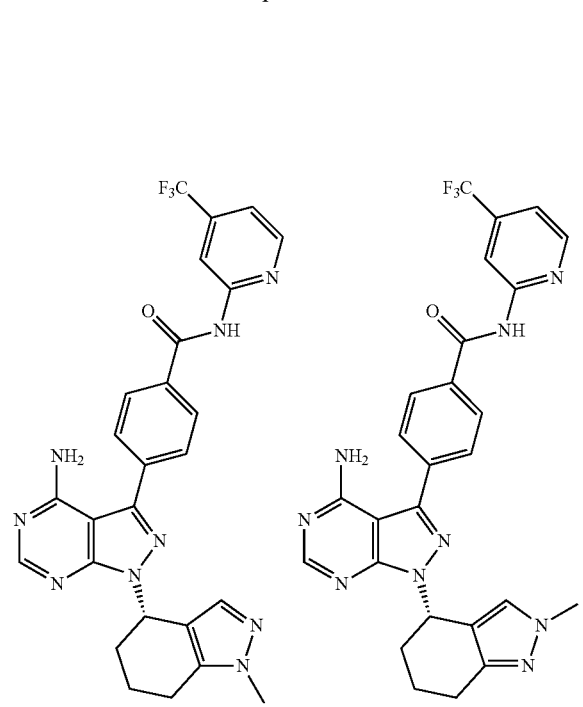

Same procedure for Example 7 and 8 afforded (S)-4-(4-amino-1-(1-methyl-4,5,6,7-tetrahydro-1H-indazol-4-yl)-1H-pyrazolo[3,4-d]pyrimidin-3-yl)-N-(4-(trifluoromethyl)pyridin-2-yl) benzamide and (S)-4-(4-amino-1-(2-methyl-4,5,6,7-tetrahydro-2H-indazol-4-yl)-1H-pyrazolo[3,4-d]pyrimidin-3-yl)-N-(4-(trifluoromethyl)pyridin-2-yl) benzamide from (S)-3-bromo-N-(2,4-dimethoxybenzyl)-1-(1-tosyl-4,5,6,7-tetrahydro-1H-indazol-4-yl)-1H-pyrazolo[3,4-d]pyrimidin-4-amine (intermediate 23E2).

Example 11 and 12

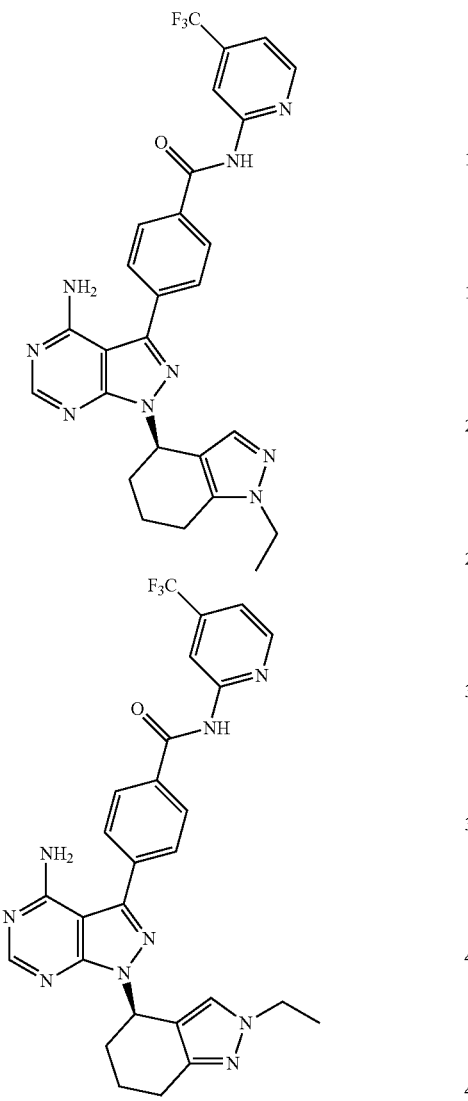

These compounds were prepared, in an analogues manner as described in Experimental 7 and 8, starting from (R)-3-bromo-N-(2,4-dimethoxybenzyl)-1-(4,5,6,7-tetrahydro-1H-indazol-4-yl)-1H-pyrazolo[3,4-d]pyrimidin-4-amine alkylating with iodoethane, to afford (R)-4-(4-amino-1-(1-ethyl-4,5,6,7-tetrahydro-1H-indazol-4-yl)-1H-pyrazolo[3,4-d]pyrimidin-3-yl)-N-(4-(trifluoromethyl)pyridin-2-yl)benzamide, $^1$H NMR (400 MHz, CD$_3$OD) δ ppm 8.62 (s, 1H), 8.65 (s, 1H), 8.46 (s, 1H), 8.14~8.16 (d, J=7.2 Hz, 2H), 7.82~7.83 (d, J=6.8 Hz, 2H), 7.44 (s, 1H), 7.14 (s, 1H), 6.21~6.22 (d, J=3.6 Hz, 1H), 4.05~4.12 (m, 2H), 2.69~2.86 (m, 2H), 2.24~2.42 (m, 3H), 1.96~2.02 (m, 1H), 1.37~1.40 (t, J=6.8 Hz, 3H). MS-ESI (m/z): 548 (M+1)$^+$.

and (R)-4-(4-amino-1-(2-ethyl-4,5,6,7-tetrahydro-2H-indazol-4-yl)-1H-pyrazolo[3,4-d]pyrimidin-3-yl)-N-(4-(trifluoromethyl)pyridin-2-yl)benzamide $^1$H NMR (400 MHz, CD$_3$OD) δ ppm 8.62 (s, 2H), 8.45 (s, 1H), 8.14~8.16 (d, J=8.4 Hz, 2H), 7.82~7.85 (d, J=8.4 Hz, 2H), 7.43~7.44 (d, J=4.4 Hz, 1H), 7.31 (s, 1H), 6.21~6.24 (t, J=5.2 Hz, 1H), 4.03~4.08 (m, 2H), 2.72~2.83 (m, 2H), 2.30~2.42 (m, 3H), 1.92~1.97 (m, 1H), 1.35~1.39 (t, J=7.2 Hz, 3H). MS-ESI (m/z): 548 (M+1)$^+$.

Example 13 and 14

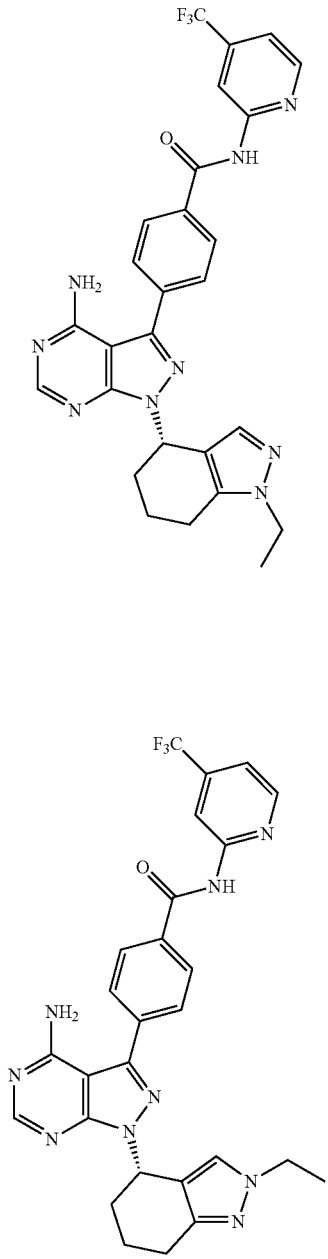

Same procedure as Example 11 and 12 afforded (S)-4-(4-amino-1-(1-ethyl-4,5,6,7-tetrahydro-1H-indazol-4-yl)-1H-pyrazolo[3,4-d]pyrimidin-3-yl)-N-(4-(trifluoromethyl)pyridin-2-yl)benzamide and (S)-4-(4-amino-1-(2-ethyl-4,5,6,7-tetrahydro-2H-indazol-4-yl)-1H-pyrazolo[3,4-d]pyrimidin-3-yl)-N-(4-(trifluoromethyl)pyridin-2-yl)benzamide.

Example 15 and 16

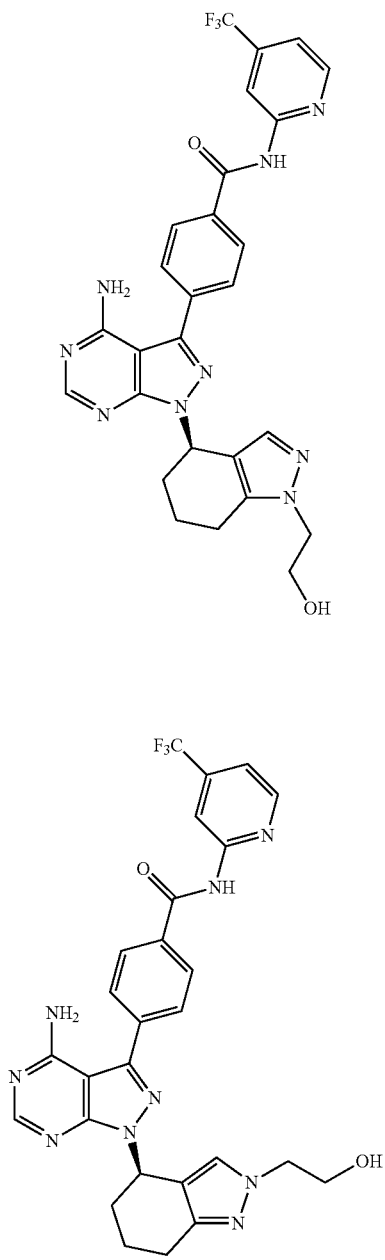

These compounds were prepared, in an analogues manner as described Example 7 and 8, starting from (R)-3-bromo-N-(2,4-dimethoxybenzyl)-1-(4,5,6,7-tetrahydro-1H-indazol-4-yl)-1H-pyrazolo[3,4-d]pyrimidin-4-amine alkylating with 2-(2-bromoethoxyl)tetrahydro-2H-pyran, to afford (R)-4-(4-amino-1-(1-(2-hydroxyethyl)-4,5,6,7-tetrahydro-1H-indazol-4-yl)-1H-pyrazolo[3,4-d]pyrimidin-3-yl)-N-(4-(trifluoromethyl)pyridin-2-yl)benzamide, ¹H NMR (400 MHz, CD₃OD) δ ppm 8.58~8.60 (d, J=5.6 Hz, 2H), 8.46 (s, 1H), 8.11~8.14 (d, J=8.4 Hz, 2H), 7.79~7.81 (d, J=8.4 Hz, 2H), 7.41~7.42 (d, J=4.8 Hz, 1H), 7.21 (s, 1H), 6.22 (m, 1H), 4.15 (m, 2H), 3.87 (m, 2H), 2.78~2.90 (m, 2H), 2.30~2.34 (m, 3H), 2.00~2.02 (m, 1H).

MS-ESI (m/z): 564 (M+1)⁺.

and (R)-4-(4-amino-1-(2-(2-hydroxyethyl)-4,5,6,7-tetrahydro-2H-indazol-4-yl)-1H-pyrazolo[3,4-d]pyrimidin-3-yl)-N-(4-(trifluoromethyl)pyridin-2-yl)benzamide ¹H NMR (400 MHz, CD₃OD) δ ppm 8.61 (s, 2H), 8.47 (s, 1H), 8.14~8.16 (d, J=7.2 Hz, 2H), 7.83~7.85 (d, J=7.2 Hz, 2H), 7.44 (s, 1H), 7.36 (s, 1H), 6.25 (m, 1H), 4.12 (m, 2H), 3.83 (m, 2H), 2.79 (m, 2H), 2.33~2.36 (m, 3H), 1.97~1.98 (m, 1H).

MS-ESI (m/z): 564 (M+1)⁺.

Example 17 and 18

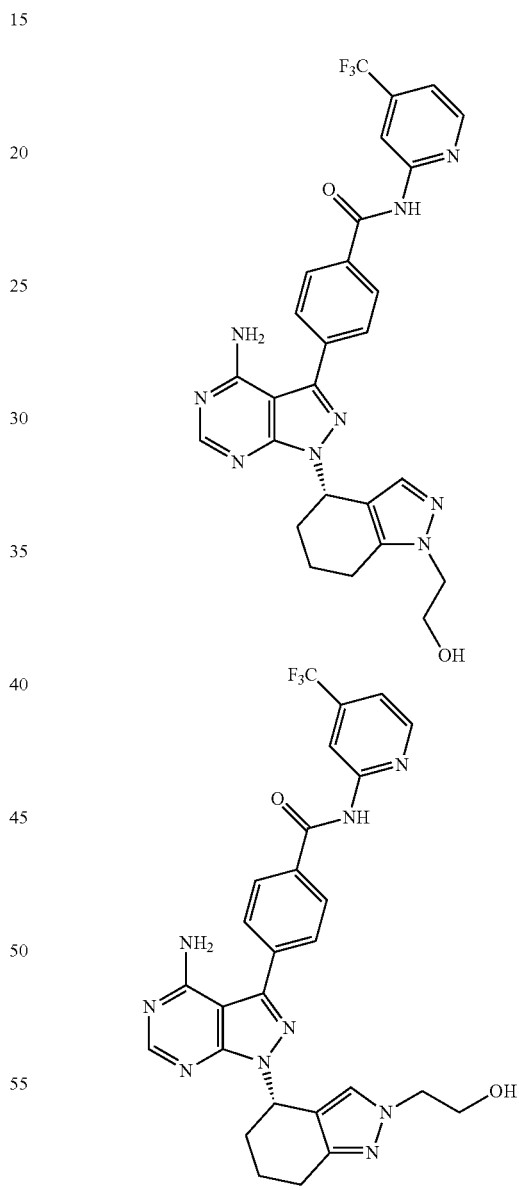

Same procedure using intermediate 23E2 afforded (S)-4-(4-amino-1-(1-(2-hydroxyethyl)-4,5,6,7-tetrahydro-1H-indazol-4-yl)-1H-pyrazolo[3,4-d]pyrimidin-3-yl)-N-(4-(trifluoromethyl)pyridin-2-yl)benzamide and (S)-4-(4-amino-1-(2-(2-hydroxyethyl)-4,5,6,7-tetrahydro-2H-indazol-4-yl)-1H-pyrazolo[3,4-d]pyrimidin-3-yl)-N-(4-(trifluoromethyl)pyridin-2-yl)benzamide.

Example 19

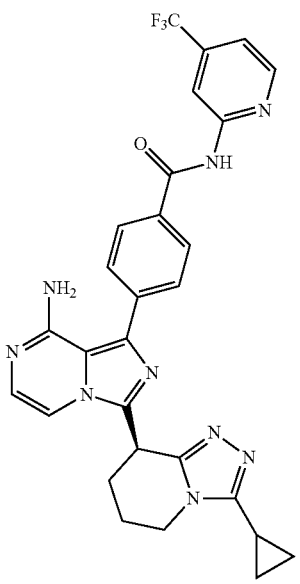 [SMILES: Nc1nccn2c([C@@H]3CCCn4c(C5CC5)nnc43)nc(-c3ccc(C(=O)Nc4cc(C(F)(F)F)ccn4)cc3)c12]

(S)-4-(8-amino-3-(3-cyclopropyl-5,6,7,8-tetrahydro-[1,2,4]triazolo[4,3-a]pyridin-8-yl) imidazo[1,5-a]pyrazin-1-yl)-N-(4-(trifluoromethyl)pyridin-2-yl)benzamide (a) (S)-methyl 4-(8-((2,4-dimethoxybenzyl)amino)-3-(2-thioxopiperidin-3-yl)imidazo[1,5-a]pyrazin-1-yl)benzoate To a solution of (S)-methyl 4-(8-((2,4-dimethoxybenzyl)amino)-3-(2-oxopiperidin-3-yl)imidazo[1,5-a]pyrazin-1-yl)benzoate (940 mg, 1.82 mmol) in toluene (25 mL) was added Lawesson's reagent (1.5 g, 3.65 mmol). The mixture was heated to reflux overnight. The solvent was evaporated and the residue was purified by column chromatography on silica gel eluted with EA:DCM:THF=1:2:1 to give (S)-methyl 4-(8-((2,4-dimethoxybenzyl)amino)-3-(2-thioxopiperidin-3-yl)imidazo[1,5-a]pyrazin-1-yl)benzoate (600 mg, yield 62%).

MS-ESI (m/z): 532 (M+1)$^+$ (Acq Method: 10-80AB_2 min; Rt: 0.94 min).

(b) (S)-methyl 4-(3-(3-cyclopropyl-5,6,7,8-tetrahydro-[1,2,4]triazolo[4,3-a]pyridin-8-yl)-8-((2,4-dimethoxybenzyl)amino)imidazo[1,5-a]pyrazin-1-yl)benzoate To a solution of (S)-methyl 4-(8-((2,4-dimethoxybenzyl)amino)-3-(2-thioxopiperidin-3-yl) imidazo[1,5-a]pyrazin-1-yl)benzoate (600 mg, 1.13 mmol) in THF (20 mL) was added cyclopropanecarbohydrazide (339 mg, 3.39 mmol) and Hg(OAc)$_2$ (360 mg, 1.13 mmol). The mixture was stirred at RT for 20 minutes and then heated to 65° C. overnight. The reaction mixture was filtered and the filtrate was evaporated, the residue was purified by column chromatography on silica gel eluted with EA:DCM:THF=1:1:1 to give (S)-methyl 4-(3-(3-cyclopropyl-5,6,7,8-tetrahydro-[1,2,4]triazolo[4,3-a]pyridin-8-yl)-8-((2,4-dimethoxybenzyl)amino)imidazo[1,5-a]pyrazin-1-yl)benzoate (300 mg, yield 46%).

MS-ESI (m/z): 580 (M+1)$^+$ (Acq Method: 10-80AB_2 min; Rt: 0.98 min).

(c) (S)-4-(3-(3-cyclopropyl-5,6,7,8-tetrahydro-[1,2,4]triazolo[4,3-a]pyridin-8-yl)-8-((2,4-di methoxybenzyl)amino)imidazo[1,5-a]pyrazin-1-yl)benzoic acid To a solution of (S)-methyl 4-(3-(3-cyclopropyl-5,6,7,8-tetrahydro-[1,2,4]triazolo[4,3-a]pyridine-8-yl)-8-((2,4-dimethoxybenzyl)amino)imidazo[1,5-a]pyrazin-1-yl)benzoate (300 mg, 0.51 mmol) in THF/MeOH/H$_2$O (3 mL/3 mL/1 mL) was added LiOH.H$_2$O (109 mg, 2.6 mmol). The mixture was stirred at RT overnight. After the reaction was completed, the reaction mixture was acidified by 2M HCl to pH=5~6 and extracted with EA and water. The organic layer was dried and concentrated to give (S)-4-(3-(3-cyclopropyl-5,6,7,8-tetrahydro-[1,2,4]triazolo[4,3-a]pyridin-8-yl)-8-((2,4-dimethoxybenzyl)amino)imidazo[1,5-a]pyrazin-1-yl)benzoic acid (130 mg, yield 45%).

MS-ESI (m/z): 566 (M+1)$^+$ (Acq Method: 10-80AB_2 min; Rt: 0.81 min).

(d) (S)-4-(3-(3-cyclopropyl-5,6,7,8-tetrahydro-[1,2,4]triazolo[4,3-a]pyridin-8-yl)-8-((2,4-di methoxybenzyl)amino)imidazo[1,5-a]pyrazin-1-yl)benzamide To a solution of (S)-4-(3-(3-cyclopropyl-5,6,7,8-tetrahydro-[1,2,4]triazolo[4,3-a]pyridin-8-yl)-8-((2,4-dimethoxybenzyl)amino)imidazo[1,5-a]pyrazin-1-yl)benzoic acid (130 mg, 0.23 mmol) in DMF (2 mL) was added NH$_4$Cl (37 mg, 0.69 mmol), TEA (93 mg, 0.92 mmol) and HATU (175 mg, 0.46 mmol). The mixture was stirred at RT overnight. After the reaction was completed, the solvent was evaporated and the residue was purified by Pre-TLC to give (S)-4-(3-(3-cyclopropyl-5,6,7,8-tetrahydro-[1,2,4]triazolo[4,3-a]pyridin-8-yl)-8-((2,4-dimethoxybenzyl)amino)imidazo[1,5-a]pyrazin-1-yl)benzamide (60 mg, yield 46%).

MS-ESI (m/z): 565 (M+1)$^+$ (Acq Method: 10-80AB_2 min; Rt: 0.76 min).

(e) (S)-4-(3-(3-cyclopropyl-5,6,7,8-tetrahydro-[1,2,4]triazolo[4,3-a]pyridin-8-yl)-8-((2,4-di methoxybenzyl)amino)imidazo[1,5-a]pyrazin-1-yl)-N-(4-(trifluoromethyl)pyridin-2-yl)benzamide To a solution of (S)-4-(3-(3-cyclopropyl-5,6,7,8-tetrahydro-[1,2,4]triazolo[4,3-a]pyridin-8-yl)-8-((2,4-dimethoxybenzyl)amino)imidazo pyrazin-1-yl)benzamide (60 mg, 0.1 mmol) in t-BuOH (4 mL) was added 2-chloro-4-(trifluoromethyl)pyridine (38 mg, 0.2 mmol), K$_3$PO$_4$ (68 mg, 0.3 mmol), Brettphos precat (1 mg) and Ruphos (1 mg). The mixture was stirred at 120° C. overnight under N$_2$. The solvent was evaporated and the residue was purified by Pre-TLC to give (S)-4-(3-(3-cyclopropyl-5,6,7,8-tetrahydro-[1,2,4]triazolo[4,3-a]pyridin-8-yl)-8-((2,4-dimethoxybenzyl)amino)imidazo[1,5-a]pyrazin-1-yl)-N-(4-(trifluoromethyl)pyridin-2-yl)benzamide (30 mg, yield 42%).

MS-ESI (m/z): 710 (M+1)$^+$ (Acq Method: 10-80AB_2 min; Rt: 1.06 min).

(f) (S)-4-(8-amino-3-(3-cyclopropyl-5,6,7,8-tetrahydro-[1,2,4]triazolo[4,3-a]pyridin-8-yl)imidazo[1,5-a]pyrazin-1-yl)-N-(4-(trifluoromethyl)pyridin-2-yl)benzamide A solution of (S)-4-(3-(3-cyclopropyl-5,6,7,8-tetrahydro-[1,2,4]triazolo[4,3-a]pyridin-8-yl)-8-((2,4-dimethoxybenzyl)amino)imidazo[1,5-a]pyrazin-1-yl)-N-(4-(trifluoromethyl)pyridin-2-yl)benzamide (30 mg, 0.04 mmol) in TFA (1.5 mL) was stirred at 110° C. for 2 hrs. The reaction mixture was purified by Pre-HPLC to give the title product.

¹H-NMR (400 MHz, CD₃OD) δ ppm 8.60 (s, 2H), 8.15 (d, J=8.4 Hz, 2H), 8.01 (d, J=5.6 Hz, 1H), 7.81 (d, J=8.4 Hz, 2H), 7.42 (d, J=5.6 Hz, 1H), 7.13 (d, J=6.0 Hz, 1H), 5.22 (t, J=8.0 Hz, 1H), 4.25~4.43 (m, 2H), 2.40~2.60 (m, 3H), 2.19~2.30 (m, 2H), 1.15~1.38 (m, 4H).

MS-ESI (m/z): 560 (M+1)⁺.

Example 20

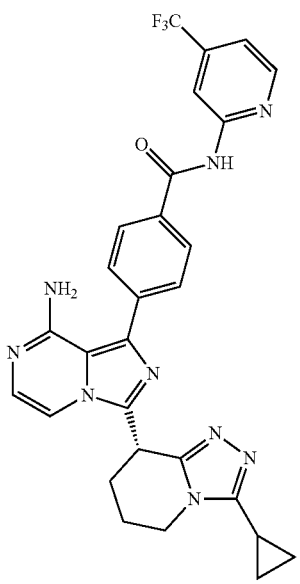 [SMILES: Nc1nccn2c([C@H]3CCCn4c(C5CC5)nnc43)nc(-c3ccc(C(=O)Nc4cc(C(F)(F)F)ccn4)cc3)c12]

Same procedure as Example 19 using intermediate 27E2, afforded (R)-4-(8-amino-3-(3-cyclopropyl-5,6,7,8-tetrahydro-[1,2,4]triazolo[4,3-a]pyridin-8-yl)imidazo[1,5-a]pyrazin-1-yl)-N-(4-(trifluoromethyl)pyridin-2-yl)benzamide. (LC-MS and NMR data WuXi)

Example 21 and 22

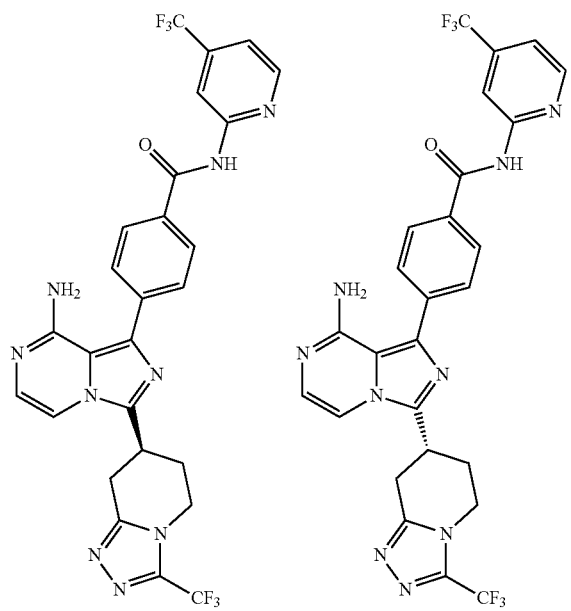 [SMILES: Nc1nccn2c([C@H]3CCn4c(nnc4C(F)(F)F)C3)nc(-c3ccc(C(=O)Nc4cc(C(F)(F)F)ccn4)cc3)c12 ; Nc1nccn2c([C@@H]3CCn4c(nnc4C(F)(F)F)C3)nc(-c3ccc(C(=O)Nc4cc(C(F)(F)F)ccn4)cc3)c12]

(S)-4-(8-amino-3-(3-(trifluoromethyl)-5,6,7,8-tetrahydro-[1,2,4]triazolo[4,3-a]pyridin-7-yl)imidazo[1,5-a]pyrazin-1-yl)-N-(4-(trifluoromethyl)pyridin-2-yl)benzamide and (R)-4-(8-amino-3-(3-(trifluoromethyl)-5,6,7,8-tetrahydro-[1,2,4]triazolo[4,3-a]pyridin-7-yl)imidazo[1,5-a]pyrazin-1-yl)-N-(4-(trifluoromethyl)pyridin-2-yl)benzamide (a) 1-tert-butyl 4-ethyl 2-oxopiperidine-1,4-dicarboxylate To a solution of the 1-tert-butyl 4-ethyl piperidine-1,4-dicarboxylate (20 g, 77.72 mmol) in CH₃CN (40 mL) and water (200 mL) at room temperature and ruthenium(IV) oxide hydrate (517.1 mg, 3.89 mmol) to give a fine black suspension. Fit a water bath at 21° C. to aid cooling. Add sodium periodate (35 g, 163.21 mmol) portion-wise over 60 minutes keeping temperature below 35° C. and only adding additional sodium periodate when the internal temperature has cooled to below 30° C. After addition is complete, the reaction was stirred at room temperature for 2 hours. Filter the mixture through a pad of filter cell and dilute the filtrate with DCM and water. Separate organic phase, dry over anhydrous Na₂SO₄, filter and concentrate to dryness under reduced pressure. Purify the crude residue by filtering through a silica gel pad (PE/EA=5/1) to provide 1-tert-butyl 4-ethyl 2-oxopiperidine-1,4-dicarboxylate as a pale yellow oil. (20 g, yield 95.6%). ¹H NMR (400 MHz, CHLOROFORM-d) δ ppm 1.15-1.26 (m, 3H) 1.46 (s, 9H) 1.84-2.02 (m, 2H) 1.84-1.85 (m, 1H) 2.06-2.17 (m, 1H) 2.67 (d, J=7.43 Hz, 2H) 2.74-2.85 (m, 1H) 3.57 (ddd, J=13.21, 8.90, 4.50 Hz, 1H) 3.67-3.75 (m, 1H) 4.12 (q, J=7.04 Hz, 2H).

(b) ethyl 2-oxopiperidine-4-carboxylate

To a solution of the 1-tert-butyl 4-ethyl 2-oxopiperidine-1,4-dicarboxylate (20 g, 74.45 mmol) in DCM (93 mL) was add 4N hydrogen chloride in dioxane (30 mL). The reaction was stirred at room temperature for 1 hour and then the solvent was removed under reduced pressure. The resulting residue was dissolved in DCM and water, then adjusted to PH=8 with saturated aqueous Na₂CO₃ solution. The mixture was extracted with DCM and the combined organic layer was washed with water, brine and dried over anhydrous Na₂SO₄. The organic layer was concentrated in vacuo to afford ethyl 2-oxopiperidine-4-carboxylate (12 g, yield 94.5%).

¹H NMR (400 MHz, CHLOROFORM-d) δ ppm 1.25 (t, J=7.04 Hz, 3H) 1.84-1.93 (m, 1H) 2.04-2.15 (m, 1H) 2.50-2.64 (m, 2H) 2.75-2.86 (m, 1H) 3.24-3.43 (m, 2H) 4.16 (q, J=7.04 Hz, 2H) 6.66 (br. s., 1H).

(c) ethyl 2-thioxopiperidine-4-carboxylate

To a solution of ethyl 2-oxopiperidine-4-carboxylate (10.76 g, 62.85 mmol) in toluene (120 mL) was added the Lawesson's reagent (25.42 g, 62.85 mmol) under a nitrogen atmosphere. The mixture was heated to reflux for 2 h. Removed the solvent under reduced pressure and the residue was purified by silica gel column chromatography (DCM/EA=20/1) to afford ethyl 2-thioxopiperidine-4-carboxylate (5.8 g, yield 49.3%).

MS-ESI (m/z): 188 (M+1)⁺ (Acq Method: 0-60AB_2 min; Rt: 0.90 min)

(d) ethyl 3-(trifluoromethyl)-5,6,7,8-tetrahydro-[1,2,4]triazolo[4,3-a]pyridine-7-carboxylate To a solution of ethyl 2-thioxopiperidine-4-carboxylate (5.7 g, 14.95 mmol) in THF (203 mL) was added 2,2,2- trifluoroacetohydrazide (7.8 g, 60.88 mmol) and Hg(OAc)$_2$ (10.71 g, 33.48 mmol) at ice-water. The mixture was stirred at room temperature for 2 hours and heated at 60° C. for overnight, then filtered. Removed the solvent under reduced pressure and the filtrate was concentrated and purified by silica gel column chromatography (PE/EA=3/1) to afford ethyl 3-(trifluoromethyl)-5,6,7,8-tetrahydro-[1,2,4]triazolo [4,3-a]pyridine-7-carboxylate (3.5 g, yield 43.8%). $^1$H NMR (400 MHz, CHLOROFORM-d) δ ppm 1.10-1.32 (m, 3H) 2.16 (br. s., 1H) 2.36 (br. s., 1H) 2.93 (br. s., 1H) 3.02-3.39 (m, 2H) 3.90-4.30 (m, 4H).

(e) 3-(trifluoromethyl)-5,6,7,8-tetrahydro-[1,2,4] triazolo[4,3-a]pyridine-7-carboxylic acid To a solution of ethyl 3-(trifluoromethyl)-5,6,7,8-tetrahydro-[1,2,4]triazolo[4,3-a]pyridine-7-carboxylate (2.28 g, 8.662 mmol) in THF (17 mL) was added 4N LiOH.H$_2$O (726.9 mg, 17.324 mmol) in water (4 mL), then the mixture was stirred at room temperature for 2 h, then acidified with 1N HCl to pH=3. The resulting mixture was extracted with EA and the aqueous phase was directly drying to give 3-(trifluoromethyl)-5,6,7,8-tetrahydro-[1,2,4]triazolo[4,3-a] pyridine-7-carboxylic acid without further purification.
MS-ESI (m/z): 236 (M+1)$^+$ (Acq Method: 0-60AB_2 min; Rt: 0.34 min)

(f) N-((3-chloropyrazin-2-yl)methyl)-3-(trifluoromethyl)-5,6,7,8-tetrahydro-[1,2,4]triazolo[4,3-a]pyridine-7-carboxamide To a solution of 3-(trifluoromethyl)-5,6,7,8-tetrahydro-[1, 2,4]triazolo[4,3-a]pyridine-7-carboxylic acid (1.63 g, 6.93 mmol) in THF (35 mL) was added dropwise (COCl)$_2$ (4.4 g, 34.66 mmol) and 0.1 mL of DMF at 0° C., the mixture was stirred at this temperature for 1 hours and then the solvent was removed. The resulting residue was dissolved in THF (35 mL), (3-chloropyrazin-2-yl)methanamine hydrochloride (1.37 g, 7.63 mmol) and DIEA (2.68 g, 20.79 mmol) was added, the mixture was stirred at 60° C. for 1 h. Remove the solvent in vacuo and the residue was extracted with DCM and the combined organic layer was washed with water, brine and dried over anhydrous Na$_2$SO$_4$. The organic layer was concentrated in vacuo and the residue was purified by silica gel column chromatography (DCM/THF=100/20) to afford N4(3-chloropyrazin-2-yl)methyl)-3-(trifluoromethyl)-5,6,7,8-tetrahydro-[1,2,4]triazolo[4,3-a]pyridine-7-carboxamide (0.8 g, yield 32%).
MS-ESI (m/z): 361 (M+1)$^+$ (Acq Method: 10-80AB_2 min; Rt: 0.81 min)

(g) 7-(8-chloroimidazo[1,5-a]pyrazin-3-yl)-3-(trifluoromethyl)-5,6,7,8-tetrahydro-[1,2,4]triazolo[4,3-a]pyridine POCl3 (1.7 g, 11.09 mmol) was added dropwise to a solution of N-((3-chloropyrazin-2-yl)methyl)-3-(trifluoromethyl)-5,6,7,8-tetrahydro-[1,2,4]triazolo[4,3-a]pyridine-7-carboxamide (800 mg, 2.218 mmol) in CH$_3$CN (4.4 mL) at 0° C., then DMF (0.11 mL) was added dropwise for 5 minutes at 0° C. The reaction was heated at 70° C. for overnight The reaction was poured into ice-water, then neutralized with aq. Na$_2$CO$_3$ to adjust to pH=8. The resulting mixture was extracted with DCM and the combined organic layer was washed with water, brine and dried over anhydrous Na$_2$SO$_4$. The organic layer was concentrated in vacuo and the residue was purified by silica gel column chromatography (DCM/THF=100/20) to afford 7-(8-chloroimidazo[1,5-a]pyrazin-3-yl)-3-(trifluoromethyl)-5,6,7,8-tetrahydro-[1,2,4]triazolo[4,3-a]pyridine (0.34 g, yield 44%).
$^1$H NMR (400 MHz, CHLOROFORM-d) δ ppm 2.38-2.56 (m, 2H) 3.25-3.54 (m, 2H) 3.65-3.75 (m, 1H) 4.09-4.22 (m, 1H) 4.32-4.42 (m, 1H) 7.37 (d, J=4.70 Hz, 1H) 7.67-7.79 (m, 2H).
MS-ESI (m/z): 343 (M+1)$^+$ (Acq Method: 10-80AB_2 min; Rt: 0.90 min)

(h) 7-(1-bromo-8-chloroimidazo[1,5-a]pyrazin-3-yl)-3-(trifluoromethyl)-5,6,7,8-tetrahydro-[1,2,4] triazolo[4,3-a]pyridine To a solution of 7-(8-chloroimidazo[1,5-a]pyrazin-3-yl)-3-(trifluoromethyl)-5,6,7,8-tetrahydro-[1,2,4]triazolo[4,3-a] pyridine (335 mg, 0.978 mmol) in DMF (4.9 mL) was added NBS (226.19 mg, 1.271 mmol) at ice water, the resulting solution was stirred at this temperature for 10 minutes. The reaction was quenched with water, then extracted with EA and the combined organic layer was washed with water, brine and dried over anhydrous Na$_2$SO$_4$. The organic layer was concentrated in vacuo to give 7-(1-bromo-8-chloroimidazo[1,5-a]pyrazin-3-yl)-3-(trifluoromethyl)-5,6,7,8-tetrahydro-[1,2,4]triazolo[4,3-a]pyridine (0.41 g, yield 99%).
MS-ESI (m/z): 422 (M+2)$^+$ (Acq Method: 10-80AB_2 min; Rt: 1.04 min)

(I) 1-bromo-3-(3-(trifluoromethyl)-5,6,7,8-tetrahydro-[1,2,4]triazolo[4,3-a]pyridin-7-yl)imidazo[1, 5-a]pyrazin-8-amine A solution of 7-(1-bromo-8-chloroimidazo[1,5-a]pyrazin-3-yl)-3-(trifluoromethyl)-5,6,7,8-tetrahydro-[1,2,4]triazolo [4,3-a]pyridine (335 mg, 0.978 mmol) in NH$_3$-iPrOH (50 mL) was heated at 100° C. for 24 hours in a sealed tube. The reaction was completed by LC-MS, then cooled to room temperature. Remove the solvent in vacuo to give 1-bromo-3-(3-(trifluoro methyl)-5,6,7,8-tetrahydro-[1,2,4]triazolo[4, 3-a]pyridin-7-yl)imidazo[1,5-a]pyrazin-8-amine as a yellow solid (0.39 g, yield 99%).
MS-ESI (m/z): 403 (M+2)$^+$ (Acq Method: 10-80AB_2 min; Rt: 0.928 min)

(J) 4-(8-amino-3-(3-(trifluoromethyl)-5,6,7,8-tetrahydro-[1,2,4]triazolo[4,3-a]pyridin-7-yl) imidazo[1, 5-a]pyrazin-1-yl)-N-(4-(trifluoromethyl)pyridin-2-yl)benzamide The mixture of 1-bromo-3-(3-(trifluoromethyl)-5,6,7,8-tetrahydro-[1,2,4]triazolo[4,3-a]pyridine-7-yl)imidazo[1,5-a]pyrazin-8-amine (200 mg, 0.497 mmol), 4-(4,4,5,5-tetramethyl-1,3,2-dioxaborolan-2-yl)-N-(4-(trifluoromethyl) pyridin-2-yl)benzamide (194.54 mg, 0.497 mmol), Pd(dppf) Cl$_2$ (18.3 mg, 0.025 mmol) and K$_2$CO$_3$ (137.26 mg, 0.995 mmol) in dioxane/H$_2$O (5 mL/0.5 mL) was stirred at 90° C. for 2 h under nitrogen atmosphere. Remove the solvent in vacuo. The mixture was treated with ethyl acetate and water, the organic layer was separated, dried over sodium sulfate, filtered and the filtrate was concentrated. The residue was purified by preparative HPLC separation to give 4-(8-amino-3-(3-(trifluoromethyl)-5,6,7,8-tetrahydro-[1,2,4]triazolo[4, 3-a]pyridin-7-yl)imidazo[1,5-a]pyrazin-1-yl)-N-(4-(trifluoromethyl)pyridin-2-yl)benzamide (0.16 g, yield 50%).
$^1$H NMR (400 MHz, METHANOL-d$_4$) δ ppm 2.39-2.62 (m, 2H) 3.45-3.60 (m, 2H) 4.06 (d, J=7.43 Hz, 1H) 4.28-4.45

(m, 2H) 7.10 (d, J=5.87 Hz, 1H) 7.43 (d, J=4.70 Hz, 1H) 7.82 (d, J=8.22 Hz, 2H) 7.95 (d, J=5.87 Hz, 1H) 8.15 (d, J=8.22 Hz, 2H) 8.61 (br. s., 2H).

(k) (S)-4-(8-amino-3-(3-(trifluoromethyl)-5,6,7,8-tetrahydro-[1,2,4]triazolo[4,3-a]pyridin-7-yl) imidazo[1,5-a]pyrazin-1-yl)-N-(4-(trifluoromethyl)pyridin-2-yl)benzamide and (R)-4-(8-amino-3-(3-(trifluoromethyl)-5,6,7,8-tetrahydro-[1,2,4]triazolo[4,3-a]pyridin-7-yl)imidazo[1,5-a]pyrazin-1-yl)-N-(4-(trifluoromethyl)pyridin-2-yl)benzamide The two enantiomers were obtained after SFC separation of 4-(8-amino-3-(3-(trifluoromethyl)-5,6,7,8-tetrahydro-[1,2,4]triazolo[4,3-a]pyridin-7-yl)imidazo[1,5-a]pyrazin-1-yl)-N-(4-(trifluoromethyl)pyridin-2-yl)benzamide.
Acq Method:
Column: Chiralpak AD-H 250×4.6 mm 5 um Mobile phase: 40% methanol (0.05% DEA) in CO2 Flow rate: 2.35 mL/min Wavelength: 220 nm
$^1$H NMR (400 MHz, METHANOL-$d_4$) δ ppm 2.39-2.59 (m, 2H) 3.49-3.62 (m, 2H) 3.98 (br. s., 1H) 4.30-4.47 (m, 2H) 7.12 (d, J=3.91 Hz, 1H) 7.42 (d, J=4.30 Hz, 1H) 7.69 (d, J=4.70 Hz, 1H) 7.80 (d, J=8.22 Hz, 2H) 8.13 (d, J=7.83 Hz, 2H) 8.54-8.68 (m, 2H). MS-ESI (m/z): 588 (M+1)$^+$.

Example 23 and 24

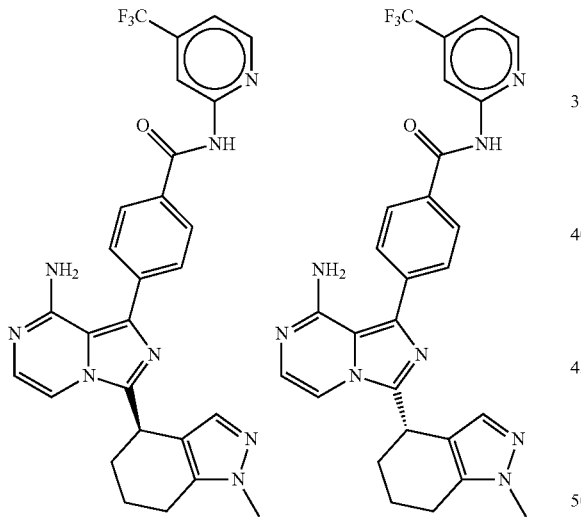

R)-4-(8-amino-3-(1-methyl-4,5,6,7-tetrahydro-1H-indazol-4-yl)imidazo[1,5-a]pyrazin-1-yl)-N-(4-(trifluoromethyl)pyridin-2-yl)benzamide and (S)-4-(8-amino-3-(1-methyl-4,5,6,7-tetrahydro-1H-indazol-4-yl)imidazo[1,5-a]pyrazin-1-yl)-N-(4-(trifluoromethyl)pyridin-2-yl)benzamide 4-(8-amino-3-(1-methyl-4,5,6,7-tetrahydro-1H-indazol-4-yl)imidazo[1,5-a]pyrazin-1-yl)-N-(4-(trifluoromethyl)pyridin-2-yl)benzamide This compound was prepared, in an analogues manner as described in example 1, starting from intermediate 4 for the Suzuki coupling, to afford the racemic title compound.

$^1$H NMR (400 MHz, CD$_3$OD): δ ppm 8.59 (s, 1H), 8.59-8.58 (d, J=5.2 Hz, 1H), 8.11-8.09 (m, 2H), 7.78-7.76 (m, 2H), 7.48-7.46 (d, J=4.2 Hz, 1H), 7.41-7.39 (d, J=3.6 Hz, 1H), 7.04 (s, 1H), 7.02-7.01 (d, J=3.6 Hz, 1H), 4.6-4.57 (m, 1H), 3.756 (s, 3H), 2.79-2.73 (m, 1H), 2.31-2.23 (m, 3H), 2.09-1.97 (m, 2H).
MS-ESI (m/z): 533 (M+1)$^+$ (Acq Method: 10-80AB_2 min_220 &254.1 cm; Rt: 0.94 min)
After separation by SFC, the two enantiomers (R)-4-(8-amino-3-(1-methyl-4,5,6,7-tetrahydro-1H-indazol-4-yl)imidazo[1,5-a]pyrazin-1-yl)-N-(4-(trifluoromethyl)pyridin-2-yl)benzamide and (S)-4-(8-amino-3-(1-methyl-4,5,6,7-tetrahydro-1H-indazol-4-yl)imidazo[1,5-a]pyrazin-1-yl)-N-(4-(trifluoromethyl)pyridin-2-yl)benzamide were obtained.
Acq Method:
Column: Chiralpak AS-H 150*4.6 mm I.D., 5 um Mobile phase: methanol (0.05% DEA) in CO2 from 5% to 40% Flow rate: 3 mL/min Wavelength: 220 nm.

Example 25

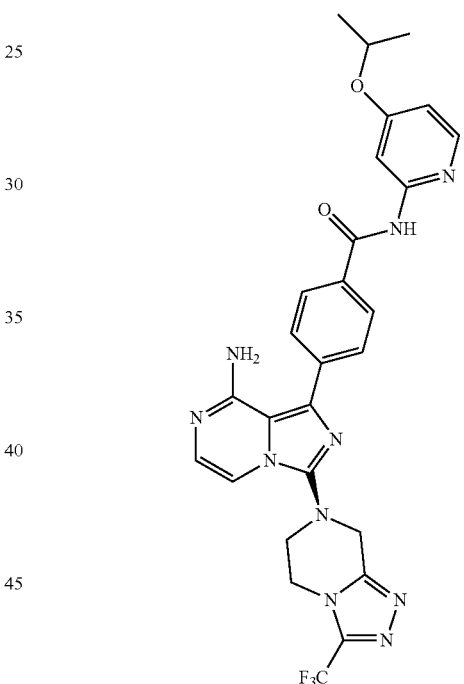

4-(8-amino-3-(3-(trifluoromethyl)-5,6-dihydro-[1,2,4]triazolo[4,3-a]pyrazin-7(8H)-yl)imidazo[1,5-a]pyrazin-1-yl)-N-(4-isopropoxypyridin-2-yl)benzamide A seal 4 ml vial containing N-(4-isopropoxypyridin-2-yl)-4-(4,4,5,5-tetramethyl-1,3,2-dioxaborolan-2-yl)benzamide, (31.3 mg, 0.082 mmol), 1-bromo-3-(3-(trifluoromethyl)-5,6-dihydro-[1,2,4]triazolo[4,3-a]pyrazin-7(8H)-yl)imidazo[1,5-a]pyrazin-8-amine, (30 mg, 0.074 mmol), and 2nd Generation Xphos Precatalyst (11.71 mg, 0.015 mmol) was treated with Dioxane (372 μl) via a syringe and needle. The resulting suspension was then degassed with house vacuum and back filled with N$_2$. Potassium phosphate tribasic (112 μl, 0.223 mmol) was then added via a syringe and needle and the resulting cream suspension stirred at 60° C. for 5 h.

Purification on the Mass Directed HPLC (method: 5 to 35% MeCN/Water w/0.05% TFA on a 30 mm×100 mm, 5 m Waters SunFire RP C-18 Column) afforded 8 mg of the Title compound as a yellow solid/LC-MS (M+1) 579.39.

Btk Enzyme Activity Assay Methods (a) Assay Method A

BTK enzymatic activity was determined in an IMAP-FP assay (Immobilized Metal ion Affinity-based fluorescence Polarization; Molecular Devices). Using this assay format, the potency ($IC_{50}$) of each compound was determined from a 10 point (1:3 serial dilution, final compound concentration range in assay from 10 µM to 0.508 nM) titration curve using the following outlined procedure. To each well of a black Corning 384-well microplate (Corning Catalog #3575), 200 nL of compound (100 fold dilution in final assay volume of 20 µL) was dispensed, followed by the addition of 10 µL of 1× kinase buffer (10 mM Tris pH 7.2, 10 mM $MgCl_2$, 0.01% Tween 20, 2 mM $MnCl_2$, and 1 mM DTT) containing 0.16 ng/µL (2.1 nM) of BTK enzyme (recombinant protein from baculovirus-transfected Sf9 cells: full-length BTK, 6HIS-tag cleaved). Following a 60 minute compound & enzyme incubation, each reaction was initiated by the addition of 10 µL kinase buffer containing 100 nM "Blk/Lyntide" IMAP substrate peptide (5-carboxyfluorescein-EFPIYDFL-PAKKK-$NH_2$; Molecular Devices Catalog #R7188), and 10 µM ATP. The final reaction in each well of 20 µL consists of 1.05 nM hBTK, 50 nM Blk/Lyntide IMAP substrate, and 5 µM ATP. Phosphorylation reactions were allowed to proceed for 120 minutes and were immediately quenched by the addition of 40 µL IMAP detection beads resuspended in IMAP progressive binding buffer (beads were diluted 1:600 in 75% and 25% progressive binding buffer A and B, respectively; Molecular Devices). Plates were read on Packard microplate reader after 60 minutes binding equilibration using Fluorescence Polarization protocol. Specifically, fluorescence at 535 nm is measured using emission filters oriented both parallel and perpendicular to the polarized excitation filter. This allows detection of changes in Fluorescence Polarization due to binding of the phosphorylated substrate peptide to the beads. Values are calculated as percentage of the difference in readout (AmP) of the controls with and without hBTK enzyme. $IC_{50}$ values are determined by curve fitting of the experimental results using Activity Base.

(b) Assay Method B

BTK enzymatic activity was determined with the LANCE (Lanthanide Chelate Excite) TR-FRET (Time-resolved fluorescence resonance energy transfer) assay. In this assay, the potency ($IC_{50}$) of each compound was determined from an eleven point (1:3 serial dilution; final compound concentration range in assay from 1 µM to 0.017 nM) titration curve using the following outlined procedure. To each well of a black non-binding surface Corning 384-well microplate (Corning Catalog #3820), 5 nL of compound (2000 fold dilution in final assay volume of 10 µL) was dispensed, followed by the addition of 7.5 µL of 1× kinase buffer (50 mM Hepes 7.5, 10 mM $MgCl_2$, 0.01% Brij-35, 1 mM EGTA, 0.05% BSA & 1 mM DTT) containing 5.09 pg/µL (66.67 pM) of BTK enzyme (recombinant protein from baculovirus-transfected Sf9 cells: full-length BTK, 6HIS-tag cleaved). Following a 60 minute compound & enzyme incubation, each reaction was initiated by the addition of 2.5 µL 1× kinase buffer containing 8 µM biotinylated "A5" peptide (Biotin-EQEDEPEGDYFEWLE-NH2), and 100 µM ATP. The final reaction in each well of 10 µL consists of 50 pM hBTK, 2 µM biotin-A5-peptide, and 25 µM ATP. Phosphorylation reactions were allowed to proceed for 120 minutes. Reactions were immediately quenched by the addition of 20 uL of 1× quench buffer (15 mM EDTA, 25 mM Hepes 7.3, and 0.1% Triton X-100) containing detection reagents (0.626 nM of LANCE-Eu-W1024-anti-phosphoTyrosine antibody, PerkinElmer and 86.8 nM of Streptavidin-conjugated Dylight 650, Dyomics/ThermoFisher Scientific). After 60 minutes incubation with detection reagents, reaction plates were read on a PerkinElmer EnVision plate reader using standard TR-FRET protocol. Briefly, excitation of donor molecules (Eu-chelate:anti-phospho-antibody) with a laser light source at 337 nm produces energy that can be transferred to Dylight-650 acceptor molecules if this donor:acceptor pair is within close proximity. Fluorescence intensity at both 665 nm (acceptor) and 615 nm (donor) are measured and a TR-FRET ratio calculated for each well (acceptor intensity/donor intensity). $IC_{50}$ values were determined by 4 parameter robust fit of TR-FRET ratio values vs. ($Log_{10}$) compound concentrations.

The following Table provides specific IC50 values for the examples. The IC50 values set forth below were determined according to Assay Method A and B described above.

| Example | IC50 BTK activity value (nM) (Method) |
|---|---|
| Example 1 | 7.2 (A) |
| Example 2 | 0.33 (B) |
| Example 3 | 2.0 (B) |
| Example 4 | 12.04 (A) |
| Example 5 | 0.52 (B) |
| Example 6 | 60 (B) |
| Example 7 | 5.9 (B) |
| Example 8 | 3.2 (B) |
| Example 9 | 2.7 (B) |
| Example 10 | 83 (B) |
| Example 11 | 3.2 (B) |
| Example 12 | 13 (B) |
| Example 13 | 5.9 (B) |
| Example 14 | 54 (B) |
| Example 15 | 1.1 (B) |
| Example 16 | 0.45 (B) |
| Example 17 | 2.1 (B) |
| Example 18 | 1.3 (B) |
| Example 19 | 67 (B) |
| Example 20 | 56 (B) |
| Example 21 | 0.81 (B) |
| Example 22 | 11 (B) |
| Example 23 | 1000 (B) |
| Example 24 | 740 (B) |
| Example 25 | 43 (B) |

What is claimed is:

1. A compound according to Formula I, or a pharmaceutically acceptable salt thereof

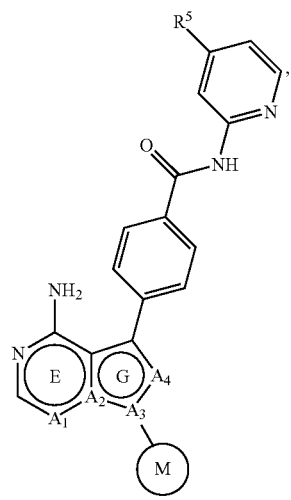

Formula I wherein:

bicyclic ring system E-G is selected from the group consisting of:

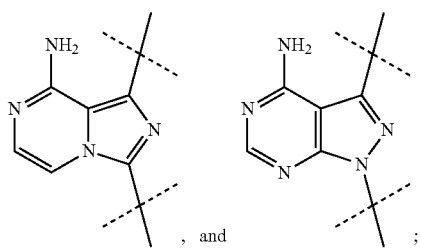
, and ;

R⁵ is H, cyano, (1-4C)alkyl, or (1-5C)alkoxy; any alkyl or alkoxy group of R⁵ may optionally be substituted with one, two or three halogen;

ring system M is selected from the group consisting of:

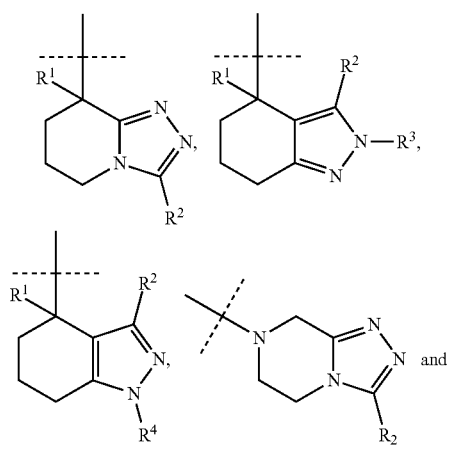

and

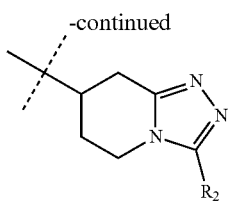

R¹ is H or OH;
R² is H, (1-3C)alkyl, cyclopropyl, or CF₃; and
R³ and R⁴ are each independently selected from H, (1-3C)alkyl, (1-3C)alkoxy, and hydroxyl(1-3C)alkyl.

2. The compound of claim 1, wherein R⁵ is selected from the group consisting of CF₃, CN and

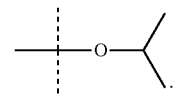

3. The compound of claim 1, wherein bicyclic ring system E-G is

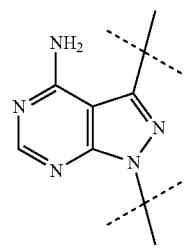

4. The compound of claim 1, wherein bicyclic ring system E-G is

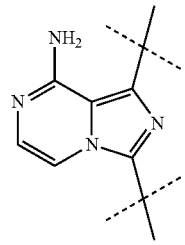

5. The compound of claim 1 selected from the group consisting of:
  4-[8-amino-3-(4-hydroxy-1-methyl-4,5,6,7-tetrahydro-1H-indazol-4-yl)imidazo[1,5-a]pyrazin-1-yl]-N-[4-(trifluoromethyl)pyridin-2-yl]benzamide;
  4-{8-amino-3-[(4S)-4-hydroxy-1-methyl-4,5,6,7-tetrahydro-1H-indazol-4-yl]imidazo[1,5-a]pyrazin-1-yl}-N-[4-(trifluoromethyl)pyridin-2-yl]benzamide;
  4-{8-amino-3-[(4R)-4-hydroxy-1-methyl-4,5,6,7-tetrahydro-1H-indazol-4-yl]imidazo[1,5-a]pyrazin-1-yl}-N-[4-(trifluoromethyl)pyridin-2-yl]benzamide;
  4-[8-amino-3-(1-ethyl-4-hydroxy-4,5,6,7-tetrahydro-1H-indazol-4-yl)imidazo[1,5-a]pyrazin-1-yl]-N-[4-(trifluoromethyl)pyridin-2-yl]benzamide;
  4-{4-amino-1-[(4S)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4R)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4R)-1-methyl-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4S)-2-methyl-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4S)-1-methyl-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4R)-2-methyl-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4S)-1-ethyl-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4S)-2-ethyl-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4R)-1-ethyl-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4R)-2-ethyl-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4S)-1-(2-hydroxyethyl)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4S)-2-(2-hydroxyethyl)-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{4-amino-1-[(4R)-1-(2-hydroxyethyl)-4,5,6,7-tetrahydro-1H-indazol-4-yl]-1H-pyrazolo[3,4-d]pyrimidin-3-yl}-N-[4-(trifluoromethyl)pyridin-2-yl]benzamide;

4-{4-amino-1-[(4R)-2-(2-hydroxyethyl)-4,5,6,7-tetrahydro-2H-indazol-4-yl]-1H-pyrazolo[3,4-d]pyrimidin-3-yl}-N-[4-(trifluoromethyl)pyridin-2-yl]benzamide;

4-{8-amino-3-[(8R)-3-cyclopropyl-5,6,7,8-tetrahydro[1,2,4]triazolo[4,3-a]pyridin-8-yl]imidazo[1,5-a]pyrazin-1-yl}-N-[4-(trifluoromethyl)pyridin-2-yl]benzamide;

4-{8-amino-3-[(8S)-3-cyclopropyl-5,6,7,8-tetrahydro[1,2,4]triazolo[4,3-a]pyridin-8-yl]imidazo[1,5-a]pyrazin-1-yl}-N-[4-(trifluoromethyl)pyridin-2-yl]benzamide;

4-{8-amino-3-[(7S)-3-(trifluoromethyl)-5,6,7,8-tetrahydro[1,2,4]triazolo[4,3-a]pyridin-7-yl]imidazo[1,5-a]pyrazin-1-yl}-N-[4-(trifluoromethyl)pyridin-2-yl]benzamide;

4-{8-amino-3-[(7R)-3-(trifluoromethyl)-5,6,7,8-tetrahydro[1,2,4]triazolo[4,3-a]pyridin-7-yl]imidazo[1,5-a]pyrazin-1-yl}-N-[4-(trifluoromethyl)pyridin-2-yl]benzamide;

4-{8-amino-3-[(4R)-1-methyl-4,5,6,7-tetrahydro-1H-indazol-4-yl]imidazo[1,5-a]pyrazin-1-yl}-N-[4-(trifluoromethyl)pyridin-2-yl]benzamide;

4-{8-amino-3-[(4S)-1-methyl-4,5,6,7-tetrahydro-1H-indazol-4-yl]imidazo[1,5-a]pyrazin-1-yl}-N-[4-(trifluoromethyl)pyridin-2-yl]benzamide; and 4-{8-amino-3-[3-(trifluoromethyl)-5,6-dihydro[1,2,4]triazolo[4,3-a]pyrazin-7(8H)-yl]imidazo[1,5-a]pyrazin-1-yl}-N-[4-(1-methylethoxyl)pyridin-2-yl]benzamide.

6. The compound of claim 1 having Formula Ia

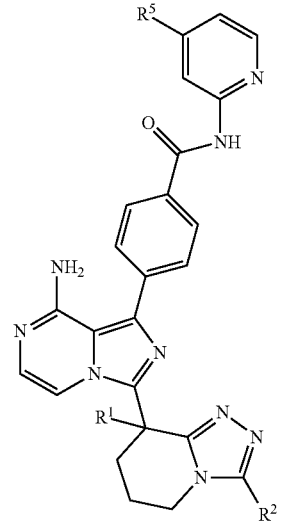

Formula Ia or a pharmaceutically acceptable salt thereof.

7. The compound of claim 1 having Formula Ib1

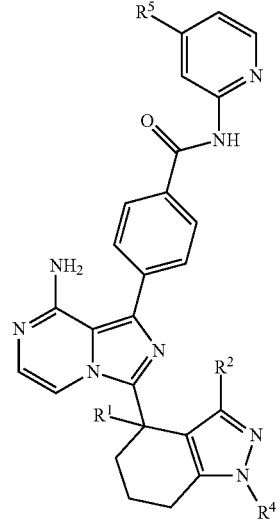

Formula Ib1 or a pharmaceutically acceptable salt thereof.

8. The compound of claim 1 having Formula Ib2
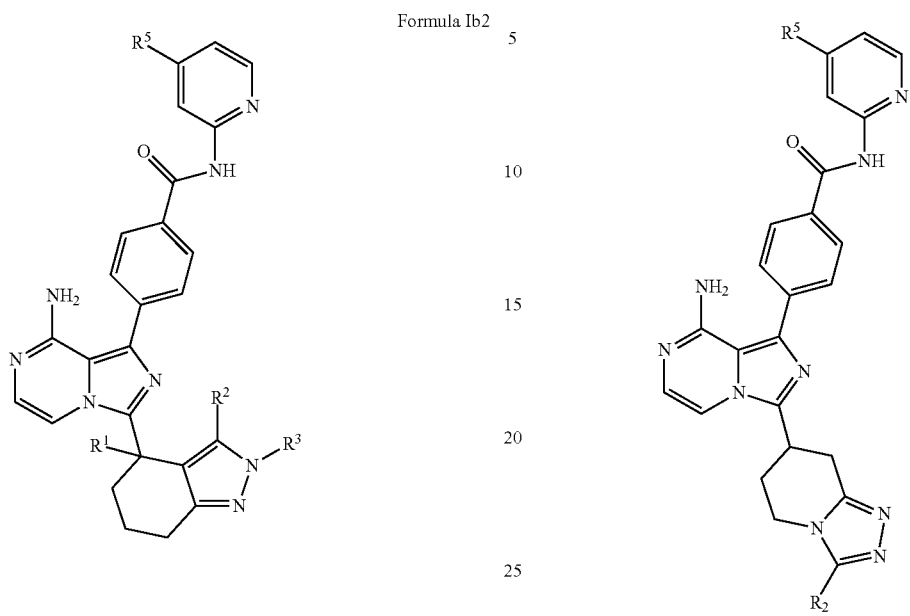
or a pharmaceutically acceptable salt thereof.
9. The compound of claim 1 having Formula Ic
10. The compound of claim 1 having Formula Id
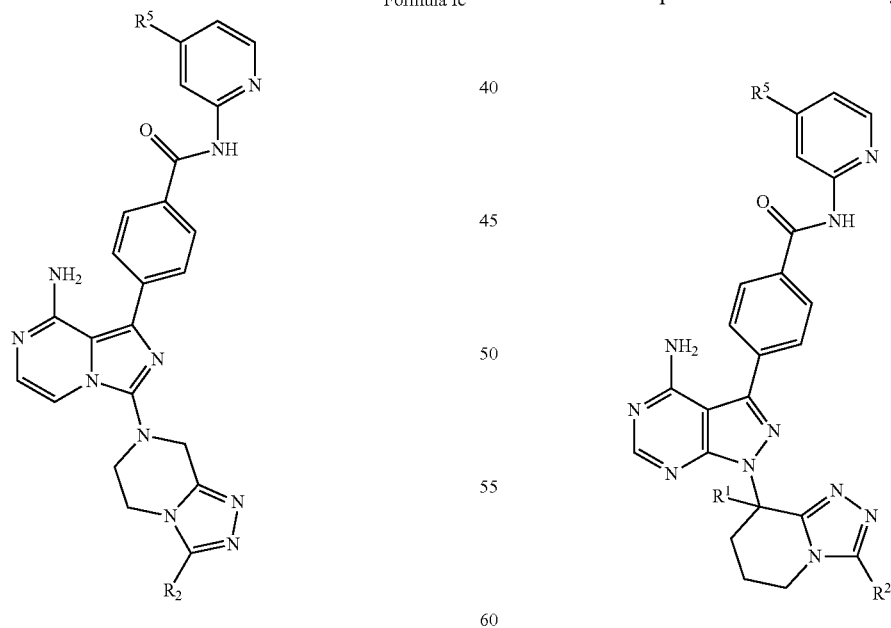
or a pharmaceutically acceptable salt thereof.
11. The compound of claim 1 having Formula Ie
or a pharmaceutically acceptable salt thereof.
or a pharmaceutically acceptable salt thereof.

12. The compound of claim 1 having Formula If1

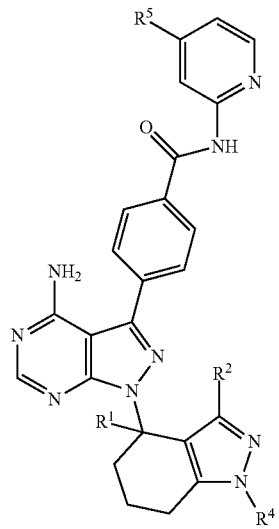

Formula If1 or a pharmaceutically acceptable salt thereof.

13. The compound of claim 1 having Formula If2

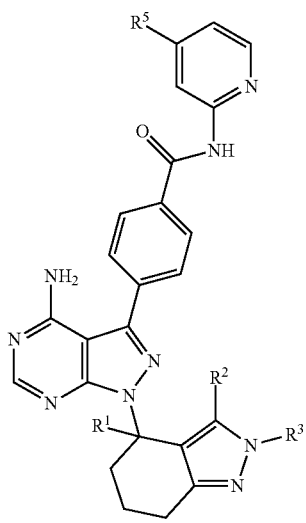

Formula If2 or a pharmaceutically acceptable salt thereof.

14. The compound of claim 1 having Formula Ig

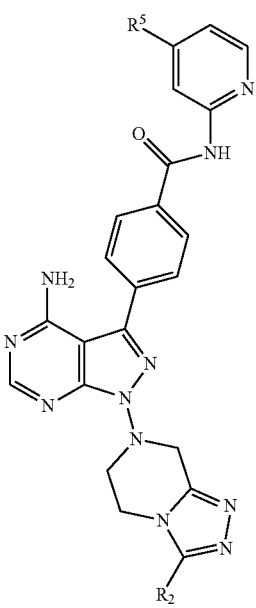

Formula Ig or a pharmaceutically acceptable salt thereof.

15. The compound of claim 1 having Formula Ih

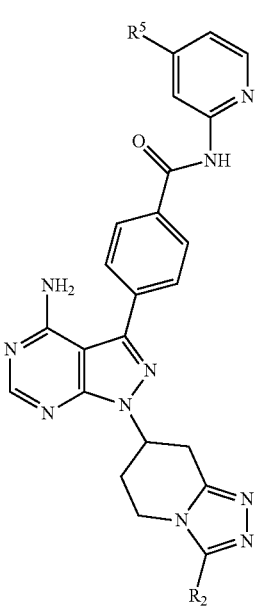

Formula Ih or a pharmaceutically acceptable salt thereof.

16. A pharmaceutical composition which comprises the compound of claim 1 or a pharmaceutically acceptable salt thereof and one or more pharmaceutically acceptable excipients.

17. The pharmaceutical composition of claim 16, which further comprises at least one additional therapeutically active agent.

18. A method for treating rheumatoid arthritis in a subject comprising administering to the subject a therapeutically effective amount of a compound of claim 1.

* * * * *